(12) United States Patent
Chang et al.

(10) Patent No.: US 9,018,233 B2
(45) Date of Patent: Apr. 28, 2015

(54) DIAMINOARYL DERIVATIVES SUBSTITUTED BY CARBAMATE AND PESTICIDAL COMPOSITION CONTAINING SAME

(71) Applicants: Kyung Nong Corporation, Seoul (KR); Korea Research Institute of Chemical Technology, Daejeon (KR)

(72) Inventors: Sung Youn Chang, Daejeon (KR); Jung Nyoung Heo, Daejeon (KR); Hyuk Lee, Seoul (KR); Hwan Jung Lim, Daejeon (KR); Bum Tae Kim, Daejeon (KR); Joo Kyung Kim, Gyeongju-si (KR); Jong-Kwan Kim, Daejeon (KR)

(73) Assignees: Kyung Nong Corporation, Seoul (KR); Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 14/395,725

(22) PCT Filed: May 7, 2013

(86) PCT No.: PCT/KR2013/003959
§ 371 (c)(1),
(2) Date: Oct. 20, 2014

(87) PCT Pub. No.: WO2013/168967
PCT Pub. Date: Nov. 14, 2013

(65) Prior Publication Data
US 2015/0094342 A1    Apr. 2, 2015

(30) Foreign Application Priority Data
May 7, 2012    (KR) ........................ 10-2012-0048226

(51) Int. Cl.
*A01N 43/40*    (2006.01)
*A01N 25/02*    (2006.01)
*A01N 25/08*    (2006.01)
*A01N 25/30*    (2006.01)
*A01N 43/56*    (2006.01)
*A61K 31/44*    (2006.01)
*C07D 401/04*    (2006.01)
*C07D 401/14*    (2006.01)
*A01N 47/20*    (2006.01)
*A01N 47/22*    (2006.01)

(52) U.S. Cl.
CPC .............. *A01N 47/20* (2013.01); *C07D 401/04* (2013.01); *A01N 47/22* (2013.01)

(58) Field of Classification Search
None
See application file for complete search history.

(56) References Cited

U.S. PATENT DOCUMENTS

2006/0167060 A1    7/2006    Lahm et al.

FOREIGN PATENT DOCUMENTS

KR    10-2007-0041744 A    4/2007
WO    2007/009661 A2    1/2007

OTHER PUBLICATIONS

International Searching Authority, International Search Report for PCT/KR2013/003959 dated Sep. 13, 2013 [PCT/ISA/210].
International Searching Authority, Written Opinion for PCT/KR2013/003959 dated Sep. 13, 2013 [PCT/ISA/237].

*Primary Examiner* — Timothy R Rozof
(74) *Attorney, Agent, or Firm* — Sughrue Mion, PLLC

(57) ABSTRACT

The invention relates to diaminoaryl derivatives substituted by carbamate, salts thereof and a pesticidal composition containing the same, which exhibit superior pest control effects against various insect pests of insect species, in particular against moths such as the diamondback moth or *Spodoptera litura*.

15 Claims, No Drawings

DIAMINOARYL DERIVATIVES SUBSTITUTED BY CARBAMATE AND PESTICIDAL COMPOSITION CONTAINING SAME

CROSS REFERENCE TO RELATED APPLICATIONS

This application is a National Stage of International Application No. PCT/KR2013/003959 filed May 7, 2013, claiming priority based on Korean Patent Application No. 10-2012-0048226 filed May 7, 2012, the contents of all of which are incorporated herein by reference in their entirety.

FIELD OF THE INVENTION

The present invention relates to diaminoaryl derivatives having pesticidal effects against harmful insects such as moths, and an insecticidal composition comprising same.

BACKGROUND OF THE INVENTION

Conventionally, carbamate- or organophosphorus-based insecticides have been widely used in the relevant field, and these insecticides produce pesticidal effects by inhibiting acetylcholinesterase (AchE). However, the extended use of such insecticides resulted in the development of resistance in the pests, which requires an insecticide having a new mechanism of action, and in response to such need, ryanodine receptors, a class of calcium ion channels have been considered as a new target for pest control.

Due to the fact that homeostasis of calcium particularly plays an important role in muscle contraction, an insecticide that binds to a ryanodine receptor inhibits feeding activities, thereby causing a coma or paralysis, and, ultimately, death in insects.

Examples of commercially available insecticides which bind to ryanodine receptors include: flubendiamide (Phoenix™, Takumi™, EP 1380209 A1, discovered by Nihon Nohyaku, co-developed with Bayer Crop Science); chlorantraniliprole having an anthranilamide structure (Rynaxypyr™, WO 01/070671, developed by DuPont); and cyantraniliprole (Cyazypyr™, WO 04/067528, developed by DuPont).

These compounds induce pesticidal effects by binding to ryanodine receptors to disturb calcium ion channels. It is known that these compounds are particularly effective against moths.

Companies including Bayer, DuPont, Syngenta, Sumitomo, Ishihara Sangyo Kaisha, Nissan, etc. have developed various derivatives of the above compounds, for which about 100 patents were granted. However, only three products, i.e., flubendiamide, chlorantraniliprole and cyantraniliprole, are currently available on the market.

Recently, in the EU, the use of neonicotinoid-based pesticides has been pointed out as one of the reasons that is responsible for the decline of the honeybee population. In January 2013, European Medicines Agency (EMA) published the result of study for issues of neonicotinoid-based pesticides. Based on the findings, the EU Commission suggested banning the use of imidacloprid, clothianidin, thiamethoxam, and decided to vote on banning the use of the products in mid-March of 2013. In Korea, there is a movement led by Rural Development Administration to redress the same issue even before environmental agencies and the National Assembly bring up the issue. As described above, there are concerns not only with the safety of humans, animals and environment in the process of developing insecticides, but with the safety of beneficial insects including honeybee. Under the circumstances, since chlorantraniliprole developed by DuPont exhibits acute contact toxicity of >4 μg/bee ($LD_{50}$), there is a need for developing an insecticide which is safer for honeybees.

Meanwhile, along with the acute contact toxicity, the half-life of residual insecticides in soil must be also taken into consideration in the process of developing an insecticide. Because the half-life of chlorantraniliprole in soil is approximately 180 days, it will remain in soil for a long time and pose a great risk to the environment. Thus, there is a great need for an environmentally friendly insecticide having a short residual period in soil, which is also safe for honeybees.

SUMMARY OF THE INVENTION

Therefore, it is an object of the present invention to provide an insecticidal composition having pesticidal effects against various harmful insects such as moths and a short residual period in soil, which is safe for beneficial insects including honeybees.

In accordance with one object of the present invention, there is provided a diaminoaryl derivative represented by formula (I) or a salt thereof:

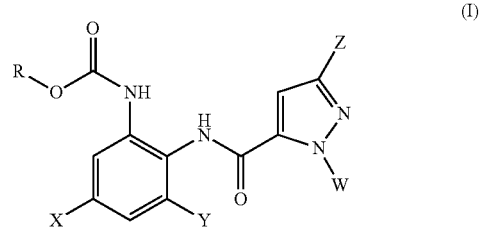

wherein X and Y are each independently hydrogen, $C_{1-6}$alkyl, $C_{2-10}$alkenyl, $C_{2-10}$alkynyl, $C_{3-6}$cycloalkyl, $C_{3-6}$cycloalkyl$C_{1-3}$alkyl, $C_{3-6}$cycloalkylamino, $C_{1-6}$alkoxy, $C_{1-5}$alkylthio, $C_{1-5}$alkylsulfinyl, $C_{1-5}$alkylsulfonyl, phenyl, phenoxy, benzyl, hydroxy, cyano, nitro or halogen, wherein each of said alkyl, alkenyl, alkynyl, cycloalkyl, alkoxy, phenyl, phenoxy and benzyl may be independently substituted with one or more halogens;

R is $C_{1-10}$alkyl, $C_{3-6}$cycloalkyl, $C_{3-6}$cycloalkyl$C_{1-3}$alkyl, $C_{2-10}$alkenyl, $C_{2-10}$alkynyl, $C_{6-12}$aryl or $C_{6-12}$aryl$C_{1-3}$alkyl, wherein each of said alkyl, cycloalkyl, alkenyl, alkynyl and aryl may be independently substituted with 1 to 5 substituents selected from the group consisting of $C_{1-5}$alkyl, halo$C_{1-5}$alkyl, $C_{1-5}$alkoxy, halo$C_{1-5}$alkoxy, $C_{1-5}$alkylamino, $C_{1-5}$alkylimino, nitro, amino, cyano, $C_{1-5}$alkylthio, $C_{1-5}$alkylsulfinyl, $C_{1-5}$alkylsulfonyl and halogen;

W is $C_{6-12}$aryl or 5 to 13-membered heteroaryl, wherein each of said aryl and heteroaryl may be independently substituted with 1 to 5 substituents selected from the group consisting of at least one halogen, $C_{1-4}$alkyl, $C_{2-5}$alkenyl, $C_{2-5}$alkynyl, $C_{1-4}$alkoxy, halo$C_{1-4}$alkyl, hydroxyl and cyano;

Z is halogen, cyano, amino, hydroxyl, mercapto, cyanothio, $C_{1-6}$alkyl, halo$C_{1-6}$alkyl, $C_{3-6}$cycloalkyl, $C_{3-6}$cycloalkyl$C_{1-3}$alkyl, $C_{2-6}$alkenyl, $C_{2-6}$alkynyl, $C_{1-6}$alkoxy, halo$C_{1-6}$alkoxy, $C_{1-5}$alkylthio, $C_{1-6}$alkylamino, $C_{1-6}$alkylimino, $C_{1-6}$alkylsulfinyl, $C_{1-6}$alkylsulfonyl, $C_{1-6}$alkylaminocarbonyl, —(CH$_2$)n-Q, —(CH$_2$)n-O-Q, —(CH$_2$)n-O—(CH$_2$)m-Q or —(CH$_2$)n-S-Q, wherein Q is phenyl, 5 to 10-membered heteroaryl or 5 to 10-membered heterocycloalkyl, and n and m are each independently integers of from 1 to 3; and said heteroaryl and heterocycloalkyl independently contain one to three heteroatoms selected from the group consisting of N, O and S.

In accordance with another object of the present invention, there is provided an insecticidal composition comprising a diaminoaryl derivative of formula (I) or a salt thereof as an active ingredient.

Further, the present invention provides a method of controlling insects, preferably moths, by applying an insecticidal composition comprising a diaminoaryl derivative of formula (I) or a salt thereof to crops or crop fields.

An insecticidal composition comprising the diaminoaryl derivative substituted by carbamate or a salt thereof according to the present invention exhibits excellent pesticidal effects against various harmful insects, particularly against moths including diamondback moth, tobacco cutworm moth, etc., while being safe for honeybees and environmentally friendly due to its short residual period in soil.

DETAILED DESCRIPTION OF THE INVENTION

Hereinafter, the compound of the present invention will be described in more detail.

In one embodiment of the compound of formula (I) or a salt thereof according to the present invention, X and Y are each independently hydrogen, $C_{1-6}$alkyl, halo$C_{1-6}$alkyl, $C_{1-6}$alkoxy, halo$C_{1-6}$alkoxy, hydroxy, cyano, nitro or halogen;

R is $C_{1-10}$alkyl, $C_{2-10}$alkenyl, $C_{6-12}$aryl or $C_{6-12}$aryl$C_{1-3}$alkyl, wherein each of said alkyl, alkenyl and aryl may independently contain 1 to 5 substituents selected from the group consisting of $C_{1-3}$alkyl, halo$C_{1-3}$alkyl, $C_{1-3}$alkoxy, halo$C_{1-3}$alkoxy, nitro and halogen;

W is $C_{6-12}$aryl, halo$C_{6-12}$aryl, 5 to 13-membered heteroaryl or 5 to 13-membered haloheteroaryl;

Z is halogen, $C_{1-6}$alkyl, halo$C_{1-6}$alkyl, $C_{1-6}$alkoxy, halo$C_{1-6}$ alkoxy, cyano or $C_{1-6}$alkylaminocarbonyl; and said heteroaryl contains one to three heteroatoms selected from the group consisting of N, O and S.

In another embodiment of the compound of formula (I) or a salt thereof,

X is hydrogen, cyano, nitro, halogen, $C_{1-5}$alkyl or halo$C_{1-5}$alkyl;

Y is $C_{1-5}$alkyl or halogen;

R is $C_{1-8}$alkyl, $C_{2-6}$alkenyl, phenyl or benzyl, wherein each of said alkyl, alkenyl, phenyl and benzyl may independently contain 1 to 3 substituents selected from the group consisting of $C_{1-3}$alkoxy, halo$C_{1-3}$alkyl, nitro and halogen;

W is phenyl, halophenyl, pyridinyl or halopyridinyl; and

Z is $C_{1-5}$alkoxy, halo$C_{1-5}$alkoxy, $C_{1-5}$alkyl, halo$C_{1-5}$alkyl, $C_{1-5}$alkylaminocarbonyl, halogen or cyano.

In still another embodiment of the compound of formula (I) or a salt thereof,

X is hydrogen, cyano, nitro, halogen or halo$C_{1-3}$alkyl;

Y is $C_{1-3}$alkyl or halogen;

R is $C_{1-8}$alkyl, $C_{2-6}$alkenyl, phenyl or benzyl, wherein each of said alkyl, alkenyl, phenyl and benzyl may independently contain 1 to 3 substituents selected from the group consisting of $C_{1-3}$alkoxy, halo$C_{1-3}$alkyl, nitro and halogen;

W is phenyl, halophenyl, pyridinyl or halopyridinyl; and

Z is $C_{1-3}$alkoxy, halo$C_{1-5}$alkoxy, halo$C_{1-3}$ alkyl, $C_{1-3}$alkylaminocarbonyl, halogen or cyano.

More specific examples of the diaminoaryl derivative of formula (I) are listed below, and a salt thereof may also be used:

1) methyl (2-(3-bromo-1-(3-chloropyridin-2-yl)-1H-pyrazole-5-carboxamido)-3,5-dichlorophenyl)carbamate;
2) ethyl (2-(3-bromo-1-(3-chloropyridin-2-yl)-1H-pyrazole-5-carboxamido)-3,5-dichlorophenyl)carbamate;
3) isopropyl (2-(3-bromo-1-(3-chloropyridin-2-yl)-1H-pyrazole-5-carboxamido)-3,5-dichlorophenyl)carbamate;
4) isobutyl (2-(3-bromo-1-(3-chloropyridin-2-yl)-1H-pyrazole-5-carboxamido)-3,5-dichlorophenyl)carbamate;
5) butyl (2-(3-bromo-1-(3-chloropyridin-2-yl)-1H-pyrazole-5-carboxamido)-3,5-dichlorophenyl)carbamate;
6) 2-bromoethyl (2-(3-bromo-1-(3-chloropyridin-2-yl)-1H-pyrazole-5-carboxamido)-3,5-dichlorophenyl)carbamate;
7) heptyl (2-(3-bromo-1-(3-chloropyridin-2-yl)-1H-pyrazole-5-carboxamido)-3,5-dichlorophenyl)carbamate;
8) allyl (2-(3-bromo-1-(3-chloropyridin-2-yl)-1H-pyrazole-5-carboxamido)-3,5-dichlorophenyl)carbamate;
9) 2-methoxyethyl (2-(3-bromo-1-(3-chloropyridin-2-yl)-1H-pyrazole-5-carboxamido)-3,5-dichlorophenyl)carbamate;
10) 3-chloropropyl (2-(3-bromo-1-(3-chloropyridin-2-yl)-1H-pyrazole-5-carboxamido)-3,5-dichlorophenyl)carbamate;
11) methyl (2-(3-bromo-1-(3-chloropyridin-2-yl)-1H-pyrazole-5-carboxamido)-5-chloro-3-methylphenyl)carbamate;
12) isobutyl (2-(3-bromo-1-(3-chloropyridin-2-yl)-1H-pyrazole-5-carboxamido)-5-chloro-3-methylphenyl)carbamate;
13) heptyl (2-(3-bromo-1-(3-chloropyridin-2-yl)-1H-pyrazole-5-carboxamido)-5-chloro-3-methylphenyl)carbamate;
14) allyl (2-(3-bromo-1-(3-chloropyridin-2-yl)-1H-pyrazole-5-carboxamido)-5-chloro-3-methylphenyl)carbamate;
15) 2-methoxyethyl (2-(3-bromo-1-(3-chloropyridin-2-yl)-1H-pyrazole-5-carboxamido)-5-chloro-3-methylphenyl) carbamate;
16) 3-chloropropyl (2-(3-bromo-1-(3-chloropyridin-2-yl)-1H-pyrazole-5-carboxamido)-5-chloro-3-methylphenyl) carbamate;
17) 2-bromoethyl (2-(3-bromo-1-(3-chloropyridin-2-yl)-1H-pyrazole-5-carboxamido)-5-chloro-3-methylphenyl)carbamate;
18) 2,2,2-trichloroethyl (2-(3-bromo-1-(3-chloropyridin-2-yl)-1H-pyrazole-5-carboxamido)-5-chloro-3-methylphenyl)carbamate;
19) 1,1,1-trichloro-2-methylpropan-2-yl (2-(3-bromo-1-(3-chloropyridin-2-yl)-1H-pyrazole-5-carboxamido)-5-chloro-3-methylphenyl)carbamate;
20) 2-fluoroethyl (2-(3-bromo-1-(3-chloropyridin-2-yl)-1H-pyrazole-5-carboxamido)-5-chloro-3-methylphenyl)carbamate;
21) ethyl (2-(3-bromo-1-(3-chloropyridin-2-yl)-1H-pyrazole-5-carboxamido)-5-chloro-3-methylphenyl)carbamate;
22) propyl (2-(3-bromo-1-(3-chloropyridin-2-yl)-1H-pyrazole-5-carboxamido)-5-chloro-3-methylphenyl)carbamate;
23) phenyl (2-(3-bromo-1-(3-chloropyridin-2-yl)-1H-pyrazole-5-carboxamido)-5-chloro-3-methylphenyl)carbamate;
24) 4-methoxyphenyl (2-(3-bromo-1-(3-chloropyridin-2-yl)-1H-pyrazole-5-carboxamido)-5-chloro-3-methylphenyl) carbamate;

25) 4-fluorophenyl (2-(3-bromo-1-(3-chloropyridin-2-yl)-1H-pyrazole-5-carboxamido)-5-chloro-3-methylphenyl)carbamate;
26) 4-chlorophenyl (2-(3-bromo-1-(3-chloropyridin-2-yl)-1H-pyrazole-5-carboxamido)-5-chloro-3-methylphenyl)carbamate;
27) 2-chlorophenyl (2-(3-bromo-1-(3-chloropyridin-2-yl)-1H-pyrazole-5-carboxamido)-5-chloro-3-methylphenyl)carbamate;
28) 4-bromophenyl (2-(3-bromo-1-(3-chloropyridin-2-yl)-1H-pyrazole-5-carboxamido)-5-chloro-3-methylphenyl)carbamate;
29) 3-(trifluoromethyl)phenyl (2-(3-bromo-1-(3-chloropyridin-2-yl)-1H-pyrazole-5-carboxamido)-5-chloro-3-methylphenyl)carbamate;
30) benzyl (2-(3-bromo-1-(3-chloropyridin-2-yl)-1H-pyrazole-5-carboxamido)-5-chloro-3-methylphenyl)carbamate;
31) 4-nitrobenzyl (2-(3-bromo-1-(3-chloropyridin-2-yl)-1H-pyrazole-5-carboxamido)-5-chloro-3-methylphenyl)carbamate;
32) 2-chlorobenzyl (2-(3-bromo-1-(3-chloropyridin-2-yl)-1H-pyrazole-5-carboxamido)-5-chloro-3-methylphenyl)carbamate;
33) methyl (2-(3-bromo-1-(3-chloropyridin-2-yl)-1H-pyrazole-5-carboxamido)-5-cyano-3-methylphenyl)carbamate;
34) isobutyl (2-(3-bromo-1-(3-chloropyridin-2-yl)-1H-pyrazole-5-carboxamido)-5-cyano-3-methylphenyl)carbamate;
35) heptyl (2-(3-bromo-1-(3-chloropyridin-2-yl)-1H-pyrazole-5-carboxamido)-5-cyano-3-methylphenyl)carbamate;
36) allyl (2-(3-bromo-1-(3-chloropyridin-2-yl)-1H-pyrazole-5-carboxamido)-5-cyano-3-methylphenyl)carbamate;
37) 2-methoxyethyl (2-(3-bromo-1-(3-chloropyridin-2-yl)-1H-pyrazole-5-carboxamido)-5-cyano-3-methylphenyl)carbamate;
38) 3-chloropropyl (2-(3-bromo-1-(3-chloropyridin-2-yl)-1H-pyrazole-5-carboxamido)-5-cyano-3-methylphenyl)carbamate;
39) 2-bromoethyl (2-(3-bromo-1-(3-chloropyridin-2-yl)-1H-pyrazole-5-carboxamido)-5-cyano-3-methylphenyl)carbamate;
40) methyl (3,5-dibromo-2-(3-bromo-1-(3-chloropyridin-2-yl)-1H-pyrazole-5-carboxamido)phenyl)carbamate;
41) isobutyl (3,5-dibromo-2-(3-bromo-1-(3-chloropyridin-2-yl)-1H-pyrazole-5-carboxamido)phenyl)carbamate;
42) heptyl (3,5-dibromo-2-(3-bromo-1-(3-chloropyridin-2-yl)-1H-pyrazole-5-carboxamido)phenyl)carbamate;
43) allyl (3,5-dibromo-2-(3-bromo-1-(3-chloropyridin-2-yl)-1H-pyrazole-5-carboxamido)phenyl)carbamate;
44) 2-methoxyethyl (3,5-dibromo-2-(3-bromo-1-(3-chloropyridin-2-yl)-1H-pyrazole-5-carboxamido)phenyl)carbamate;
45) 3-chloropropyl (3,5-dibromo-2-(3-bromo-1-(3-chloropyridin-2-yl)-1H-pyrazole-5-carboxamido)phenyl)carbamate;
46) 2-bromoethyl (3,5-dibromo-2-(3-bromo-1-(3-chloropyridin-2-yl)-1H-pyrazole-5-carboxamido)phenyl)carbamate;
47) isobutyl (5-bromo-2-(3-bromo-1-(3-chloropyridin-2-yl)-1H-pyrazole-5-carboxamido)-3-methylphenyl)carbamate;
48) methyl (2-(3-bromo-1-(3-chloropyridin-2-yl)-1H-pyrazole-5-carboxamido)-3-chloro-5-(trifluoromethyl)phenyl)carbamate;
49) isobutyl (2-(3-bromo-1-(3-chloropyridin-2-yl)-1H-pyrazole-5-carboxamido)-3-chloro-5-(trifluoromethyl)phenyl)carbamate;
50) heptyl (2-(3-bromo-1-(3-chloropyridin-2-yl)-1H-pyrazole-5-carboxamido)-3-chloro-5-(trifluoromethyl)phenyl)carbamate;
51) methyl (3-bromo-2-(3-bromo-1-(3-chloropyridin-2-yl)-1H-pyrazole-5-carboxamido)-5-(trifluoromethyl)phenyl)carbamate;
52) isobutyl (3-bromo-2-(3-bromo-1-(3-chloropyridin-2-yl)-1H-pyrazole-5-carboxamido)-5-(trifluoromethyl)phenyl)carbamate;
53) heptyl (3-bromo-2-(3-bromo-1-(3-chloropyridin-2-yl)-1H-pyrazole-5-carboxamido)-5-(trifluoromethyl)phenyl)carbamate;
54) methyl (2-(3-bromo-1-(3-chloropyridin-2-yl)-1H-pyrazole-5-carboxamido)-3-methylphenyl)carbamate;
55) methyl (2-(3-bromo-1-(3-chloropyridin-2-yl)-1H-pyrazole-5-carboxamido)-3-methyl-5-nitrophenyl)carbamate;
56) methyl (2-(3-chloro-1-(3-chloropyridin-2-yl)-1H-pyrazole-5-carboxamido)-5-cyano-3-methylphenyl)carbamate;
57) methyl (2-(1-(3-chloropyridin-2-yl)-3-cyano-1H-pyrazole-5-carboxamido)-5-cyano-3-methylphenyl)carbamate;
58) methyl (2-(1-(3-chloropyridin-2-yl)-3-methoxy-1H-pyrazole-5-carboxamido)-5-cyano-3-methylphenyl)carbamate;
59) methyl (2-(1-(3-chloropyridin-2-yl)-$N^3$-methyl-1H-pyrazole-3,5-dicarboxamido)-5-cyano-3-methylphenyl)carbamate;
60) methyl (2-(3-(2,2,2-trifluoroethoxy)-1-(3-chloropyridin-2-yl)-1H-pyrazole-5-carboxamido)-5-cyano-3-methylphenyl)carbamate;
61) methyl (2-(1-(3-chloropyridin-2-yl)-3-(trifluoromethyl)-1H-pyrazole-5-carboxamido)-5-cyano-3-methylphenyl)carbamate;
62) methyl (2-(1-(2-chlorophenyl)-3-(trifluoromethyl)-1H-pyrazole-5-carboxamido)-5-cyano-3-methylphenyl)carbamate;
63) ethyl (2-(3-bromo-1-(3-chloropyridin-2-yl)-1H-pyrazole-5-carboxamido)-5-cyano-3-methylphenyl)carbamate; and
64) 2-chloroethyl (2-(3-bromo-1-(3-chloropyridin-2-yl)-1H-pyrazole-5-carboxamido)-5-cyano-3-methylphenyl)carbamate.

In addition to the compound of formula (I) as described above, a salt thereof may also fall under the scope of the present invention. A salt of the compound of the present invention is preferably agriculturally acceptable inorganic or organic salt, for example, an acid addition salt formed by bromic acid, hydrochloric acid, nitric acid, phosphoric acid, sulfuric acid, acetic acid, butyric acid, fumaric acid, lactic acid, maleic acid, malonic acid, oxalic acid, propionic acid, salicylic acid, tartaric acid, 4-toluensulfonic acid or valeric acid.

Further, the present invention provides an insecticidal composition comprising an effective amount of the carbamate-substituted diaminoaryl derivative of formula (I) or a salt thereof as an active ingredient and a carrier. The carrier may be any agriculturally acceptable carrier, for example, kaolin, talc, dolomite, pyrophyllite, diatomaceous earth, calcium carbonate, etc.

Furthermore, the present invention provides a method of controlling harmful insects by applying the compound of formula (I) or a salt thereof to crops or crop fields. The harmful insects are preferably moths, and more specifically diamondback moth, tobacco cutworm moth and the like.

The diaminoaryl derivative substituted by carbamate according to the present invention and an insecticidal composition comprising same exhibit excellent pesticidal effects against various harmful insects, particularly against moths including diamondback moth, tobacco cutworm moth, etc., but are safe for beneficial insects including honeybee, etc.

Hereinafter, a method for preparing the carbamate-substituted diaminoaryl derivative of the present invention is explained in more detail.

In one embodiment, the compound of formula (I) of the present invention may be prepared according to the procedure shown in Reaction Scheme 1 below:

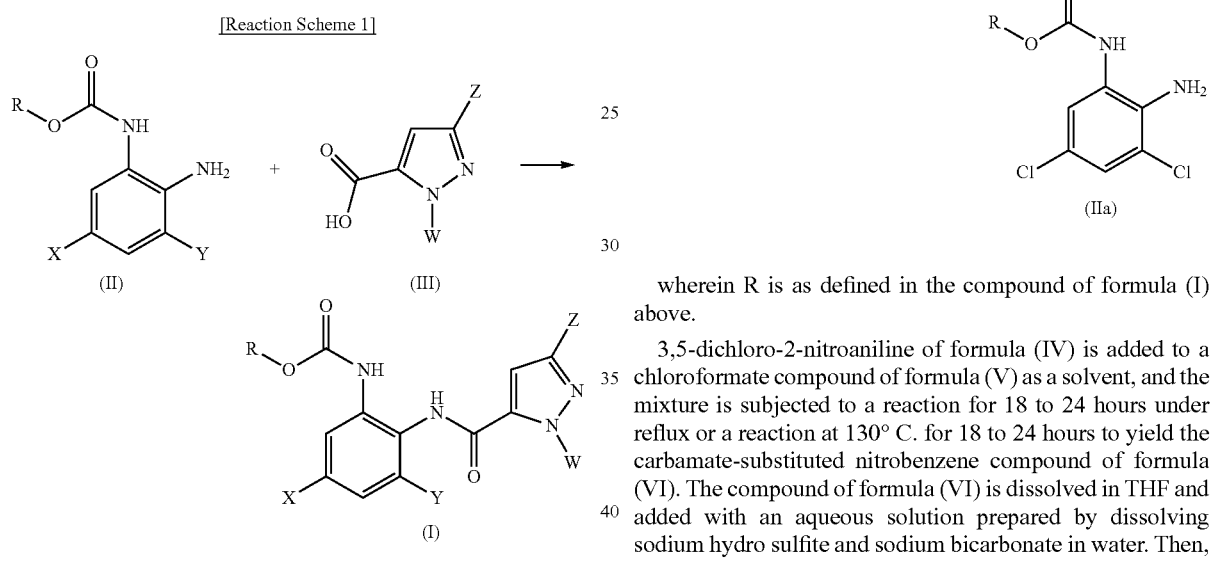

wherein X, Y, Z, W and R are as defined in the compound of formula (I) above.

An aniline compound of formula (II) and a carboxylic acid of formula (III) are dissolved in acetonitrile, and 3-picoline is added thereto. After 5 to 30 minutes, methanesulfonyl chloride is slowly added to the mixture, which is then subjected to a reaction at a temperature of from room temperature to 40° C. for 20 to 24 hours to yield the compound of formula (I).

In the case where the starting material is an aniline compound in which X is CN, trifluoromethanesulfonyl chloride may be used instead of methanesulfonyl chloride.

The compound of formula (III) may be prepared by conventional methods disclosed in Lahm, George P. et al., *Bioorganic and Medicinal Chemistry Letters,* 2007, vol. 17, #22, pp. 6274-6279; Feng, Q. et. al. *J. Agric. Food. Chem.* 2010, 58, pp. 12327-12336; *J. Agric. Food Chem.* 2012, 60, pp. 7565-7572; *Chin. J. Chem.* 2010, 28, pp. 1757-1760; *Chin. J. Chem.* 2012, 30, pp. 1748-1758; US 2010/273830 A1; WO 2008/73873 A1; and WO 2003/106427 A2.

In one embodiment, the aniline compound of formula (II), which is a starting material of Reaction Scheme I, may be prepared according to the procedure shown in Reaction Scheme 2 below:

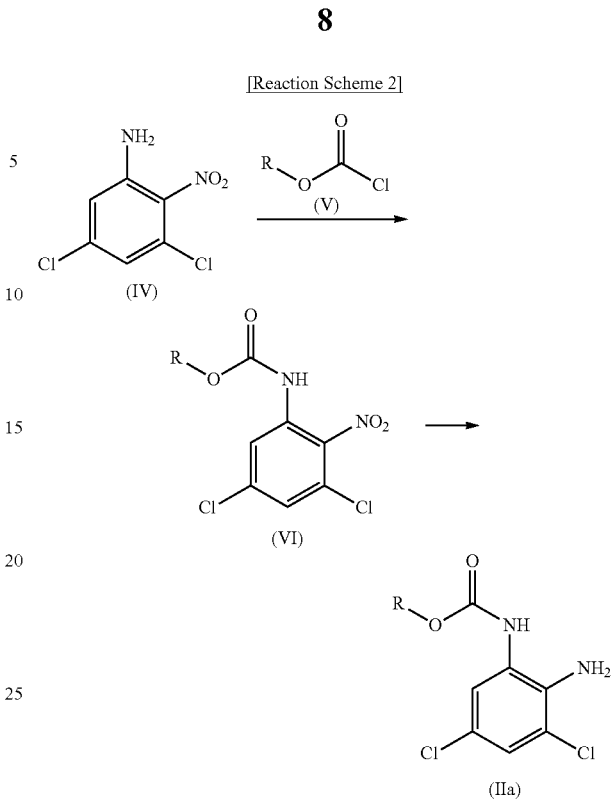

wherein R is as defined in the compound of formula (I) above.

3,5-dichloro-2-nitroaniline of formula (IV) is added to a chloroformate compound of formula (V) as a solvent, and the mixture is subjected to a reaction for 18 to 24 hours under reflux or a reaction at 130° C. for 18 to 24 hours to yield the carbamate-substituted nitrobenzene compound of formula (VI). The compound of formula (VI) is dissolved in THF and added with an aqueous solution prepared by dissolving sodium hydro sulfite and sodium bicarbonate in water. Then, the mixture is subjected to a reaction at room temperature for 2 to 4 hours to yield the carbamate-substituted aniline compound of formula (IIa).

During this process, the 3,5-dichloro-2-nitroaniline of formula (IV) may be prepared by the method disclosed by Vasiliki Giannouli et al, Design, Synthesis, and Evaluation of the Antiproliferative Activity of a Series of Novel Fused Xanthenone amino derivatives in Human Breast Cancer Cells, *Journal of medicinal Chemistry,* 50(7), pp. 1716-1719, 2007.

In one embodiment, the aniline compound of formula (II), which is a starting material of Reaction Scheme I, may be prepared according to the procedure shown in Reaction Scheme 3 below:

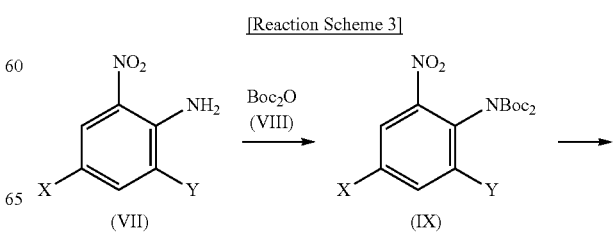

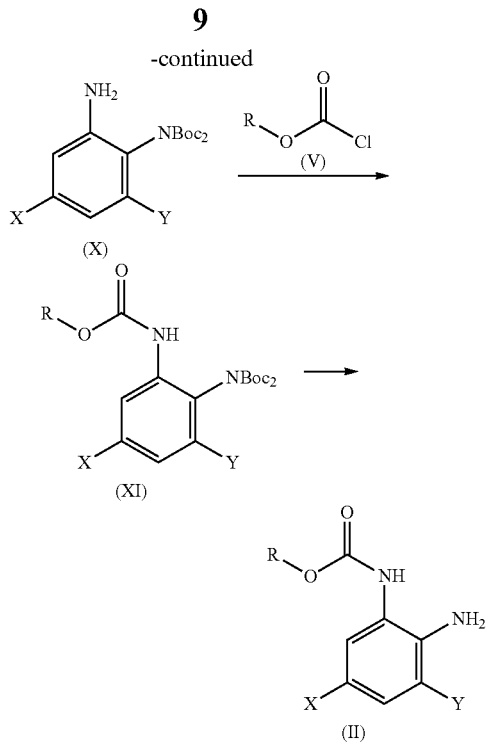

wherein X, Y and R is as defined in the compound of formula (I) above.

The nitroaniline compound of formula (VII) is dissolved in THF and added with di-t-butyl dicarbonate. After adding 4-dimethylaminopyridine as a catalyst, the mixture is subjected to a reaction for 1 to 5 hours under reflux to yield the Boc-protected nitroaniline compound of formula (IX). The compound of formula (VII) in which X is CN and Y is Me, i.e., 4-amino-3-methyl-5-nitrobenzonitrile, may be prepared by the method disclosed in WO 2007/56155 A1 (Chembridge Research Laboratories, Inc.). The compound of formula (VII) having other X and Y substituents may be prepared by conventional methods.

The nitroaniline compound of formula IX is dissolved in ethanol, added with tin chloride, and stirred for 2 to 4 hours at room temperature to yield the Boc-protected aniline compound of formula (X). Alternatively, the nitroaniline compound of formula (IX) is dissolved in THF and added with an aqueous solution prepared by dissolving sodium hydrosulfite and sodium bicarbonate in water, and the mixture is subjected to a reaction at room temperature for 1 to 4 hours to yield the aniline compound of formula (X).

The aniline compound of formula (X) is added with the chloroformate compound of formula (V) and pyridine, and the mixture is stirred at 80° C. for 2 to 24 hours to yield the carbamate-substituted Boc-protected compound of formula (XI). Meanwhile, in the case where the chloroformate compound is 2-bromoethyl chloroformate, the aniline compound of formula (X) is dissolved in dichloromethane and added with pyridine and 2-bromoethyl chloroformate, and the mixture is stirred at room temperature for 4 to 24 hours to yield the carbamate-substituted compound of formula (XI).

The compound of formula (XI) is dissolved in dichloromethane and added with TFA, and the mixture is stirred at room temperature for 1 to 8 hours to obtain the carbamate-substituted aniline compound of formula (II).

The following Examples are provided to illustrate preferred embodiments of the present invention, and are not intended to limit the scope of the present invention.

Example 1

Methyl (2-(3-bromo-1-(3-chloropyridin-2-yl)-1H-pyrazole-5-carboxamido)-3,5-dichlorophenyl)carbamate Step 1. Methyl (3,5-dichloro-2-nitrophenyl)carbamate 3,5-Dichloro-2-nitroaniline (600 mg, 2.90 mmol) was added with methyl chloroformate (25 mL, 0.12 M), and the mixture was subjected to a reaction for 18 hours under reflux. Methyl chloroformate was removed under reduced pressure, and the compound thus obtained was purified by column chromatography using 10% EtOAc/hexane to obtain the title compound (480 mg, yield: 63%).

In this step, the starting material, 3,5-dichloro-2-nitroaniline, was synthesized by using the method disclosed in Vasiliki Giannouli et al, Design, Synthesis, and Evaluation of the Antiproliferative Activity of a Series of Novel Fused Xanthenone aminoderivatives in Human Breast Cancer Cells, Journal of medicinal Chemistry, 50(7), pp. 1716-1719, 2007.

$^1$H-NMR (300 MHz, CDCl$_3$) δ 8.25 (d, 1H, J=2.0 Hz), 7.72 (brs, 1H), 7.24 (d, 1H, J=2.1 Hz), 3.82 (s, 3H).

Step 2. Methyl (2-amino-3,5-dichlorophenyl)carbamate

Methyl (3,5-dichloro-2-nitrophenyl)carbamate (79 mg, 0.3 mmol) prepared in Step 1 was added with THF (1.5 mL, 0.2 M), followed by stirring. In a separate vial, sodium hydrosulfite (603 mg, 2.7 mmol, 9.0 eq) and sodium bicarbonate (227 mg, 2.7 mmol, 9.0 eq) were dissolved in H$_2$O (3 mL, 0.1 M), and the solution thus obtained was added to a solution of methyl (3,5-dichloro-2-nitrophenyl)carbamate. MeOH (0.5 mL) was added to the solution, and the mixture was subjected to a reaction at room temperature for 2 hours. Upon completion of the reaction, THF and MeOH were removed by distillation under reduced pressure, and the residue thus obtained was extracted with ethyl acetate (30 mL x 2), dried over MgSO$_4$, and concentrated under reduced pressure. Subsequently, the residue was purified by silica gel column chromatography (EtOAc/Hex=1:4) to obtain the title compound (30 mg, yield: 43%).

$^1$H NMR (300 MHz, CDCl$_3$) δ 7.34 (s, 1H), 7.15 (s, 1H), 6.41 (s, 1H), 4.04 (s, 2H), 3.79 (s, 3H).

Step 3. Methyl (2-(3-bromo-1-(3-chloropyridin-2-yl)-1H-pyrazole-5-carboxamido)-3,5-dichlorophenyl)carbamate 3-Bromo-1-(3-chloropyridin-2-yl)-1H-pyrazole-5-carboxylic acid (100 mg, 0.33 mmol) and methyl (2-amino-3,5-dichlorophenyl)carbamate prepared in Step 2 (77 mg, 0.33 mmol, 1.0 eq) were mixed with 1 mL of CH$_3$CN. 3-Picoline (0.07 mL, 0.66 mmol, 2.0 eq) was added to the mixture thus obtained, followed by stirring for 30 minutes. After 30 minutes, methanesulfonyl chloride (0.04 mL, 0.5 mmol, 1.5 eq) was slowly added to the mixture. Upon completion of the dropwise addition, the mixture was heated to 40° C. and subjected to a reaction for 24 hours. After confirming the termination of the reaction by using TLC, the solvent was removed, and the residue thus obtained was purified by column chromatography using 20% EtOAc/hexane solution, 50% EtOAc/hexane solution and 100% EtOAc in turn to yield the title compound (130 mg, yield: 75%).

In this step, one of the starting material, 3-bromo-1-(3-chloropyridin-2-yl)-1H-pyrazole-5-carboxylic acid, was synthesized by using the method disclosed in Lahm, George P. et al., Rynaxypyr: a new insecticidal anthranilic diamide that acts as a potent and selective ryanodine receptor activator, *Bioorganic and Medicinal Chemistry Letters*, 2007, vol. 17, #22, pp. 6274-6279 or WO 2003/106427 A2 (E.I. DUPONT DE NEMOURS AND COMPANY et al.).

$^1$H-NMR (300 MHz, DMSO-$d_6$) δ 10.12 (brs, 1H), 9.51 (brs, 1H), 8.50 (d, 1H, J=4.7 Hz), 8.17 (d, 1H, J=8.1 Hz), 7.90 (s, 1H), 7.62 (q, 1H, J=4.3 Hz), 7.43 (s, 1H), 7.39 (s, 1H), 3.68 (s, 3H).

Examples 2 to 10

The procedure of Example 1 including Steps 1 to 3 was repeated except for using the corresponding R-chloroformate in which R is a substituent shown in Table 1, instead of methyl chloroformate in Step 1, to obtain the title compounds of Examples 2 to 10.

The compounds obtained in Examples 1 to 10 have the following base structures, and each corresponding substituents and $^1$H NMR data are shown in Table 1 below:

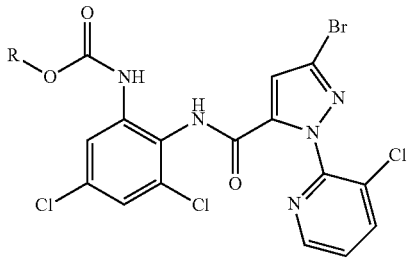

TABLE 1

| Example | R | $^1$H NMR |
|---|---|---|
| 1 | Me | $^1$H NMR(300 MHz, DMSO-$d_6$) δ 10.12(brs, 1H), 9.51(brs, 1H), 8.50(d, 1H, J = 4.7 Hz), 8.17(d, 1H, J = 8.1 Hz), 7.90(s, 1H), 7.62(q, 1H, J = 4.3 Hz), 7.43(s, 1H), 7.39(s, 1H), 3.68(s, 3H) |
| 2 | Et | $^1$H NMR(300 MHz, DMSO-$d_6$) δ 10.11(brs, 1H), 9.46(s, 1H), 8.50(d, 1H, J = 4.5 Hz), 8.18(d, 1H, J = 8.0 Hz), 7.93(d, 1H, J = 1.9 Hz), 7.62(dd, 1H, J = 8.1 Hz, 4.7 Hz), 7.45(s, 1H), 7.39(d, 1H, J = 2.2 Hz), 4.13(q, 2H, J = 7.1 Hz), 1.23(t, 3H, J = 7.0 Hz) |
| 3 | i-Pr | $^1$H NMR(300 MHz, CDCl$_3$) δ 8.51(d, 1H, J = 3.7 Hz), 8.02(s, 1H), 7.91(d, 1H, J = 8.1 Hz), 7.82(s, 1H), 7.42(dd, 1H, J = 8.0 Hz, 4.6 Hz), 7.22(d, 1H, J = 1.3 Hz), 7.11(s, 1H), 7.03(s, 1H), 4.99(sep, 1H, J = 6.3 Hz), 1.30(d, 6H, J = 6.2 Hz) |
| 4 | i-Bu | $^1$H NMR(300 MHz, CDCl$_3$) δ 8.46(s, 1H), 8.32(s, 1H), 7.89(d, J = 8.0 Hz, 1H), 7.73(s, 1H), 7.40(dd, J = 7.3, 4.1 Hz, 1H), 7.27(s, 1H), 7.18(s, 1H), 7.07(s, 1H), 3.92(d, J = 6.7 Hz, 2H), 1.95(dt, J = 13.4, 6.6 Hz, 1H), 0.95(d, J = 6.5 Hz, 6H). |
| 5 | n-Bu | $^1$H NMR(300 MHz, DMSO) δ 10.14(s, 1H), 9.47(s, 1H), 8.51(d, J = 4.0, 1H), 8.18(d, J = 8.0, 1H), 7.91(s, 1H), 7.63(dd, J = 7.6, 4.8, 1H), 7.47(s, 1H), 7.41(d, J = 1.6, 1H), 4.10(t, J = 6.4, 2H), 1.63-1.56(m, 2H), 1.35(dd, J = 14.9, 7.3, 2H), 0.90(t, J = 7.2, 3H). |
| 6 | BrCH$_2$CH$_2$— | $^1$H NMR(300 MHz, CDCl$_3$) δ 8.52(s, 1H), 7.96(m, 2H), 7.82(s, 1H), 7.43(m, 1H), 7.38(s, 1H), 7.24(s, 1H), 7.03(s, 1H), 4.47(t, J = 6.4 Hz, 2H), 3.55(t, J = 6.4 Hz, 2H). |
| 7 | n-Heptyl | $^1$H NMR(300 MHz, CDCl$_3$) δ 8.49(d, J = 4.9 Hz, 1H), 8.02(s, 1H), 7.91(d, J = 8.2 Hz, 1H), 7.79(s, 1H), 7.41(dd, J = 8.0, 4.6 Hz, 1H), 7.22(s, 1H), 7.16(s, 1H), 7.02(s, 1H), 4.14(t, J = 6.8 Hz, 2H), 1.72-1.62(m, 2H), 1.38-1.22(m, 8H), 0.93-0.84(m, 3H). |
| 8 | CH$_2$=CHCH$_2$— | $^1$H NMR(300 MHz, CDCl$_3$) δ 8.48(d, J = 4.5 Hz, 1H), 8.02(s, 1H), 7.92(d, J = 8.1 Hz, 1H), 7.81(s, 1H), 7.40(dd, J = 8.0, 4.7 Hz, 1H), 7.29(s, 1H), 7.24(s, 1H), 7.02(s, 1H), 6.00-5.90(m, 1H), 5.36(d, J = 16.9 Hz, 1H), 5.29(d, J = 10.6 Hz, 1H), 4.66(d, J = 5.6 Hz, 2H). |
| 9 | CH$_3$OCH$_2$CH$_2$— | $^1$H NMR(300 MHz, CDCl$_3$) δ 8.52(d, J = 4.5 Hz, 1H), 8.02(s, 1H), 7.93(d, J = 7.9 Hz, 1H), 7.79(s, 1H), 7.40(dd, J = 7.8, 4.8 Hz, 1H), 7.23(s, 1H), 7.01(s, 1H), 4.31(t, J = 4.5 Hz, 2H), 3.63(t, J = 4.5 Hz, 2H), 3.40(d, J = 1.2 Hz, 3H). |
| 10 | ClCH$_2$CH$_2$— | $^1$H NMR(300 MHz, CDCl$_3$) δ 8.49(d, J = 4.2 Hz, 1H), 8.00(s, 1H), 7.93(d, J = 8.1 Hz, 1H), 7.82(s, 1H), 7.44(dd, J = 8.1, 4.9 Hz, 1H), 7.30(s, 1H), 7.24(s, 1H), 7.03(s, 1H), 4.32(t, J = 6.0 Hz, 2H), 3.62(t, J = 6.4 Hz, 2H), 2.14(p, J = 6.4 Hz, 2H). |

Examples 11 to 20

Steps 1 to 5 of Example 35 as described below were repeated except for using 4-chloro-2-methyl-6-nitroaniline instead of 4-amino-3-methyl-5-nitrobenzonitrile as a starting material in Step 1 and using the corresponding R-chloroformate in which R is a substituent shown in Table 2, instead of heptyl chloroformate in Step 3, to obtain the title compounds of Examples 11 to 20. In this process, 4-chloro-2-methyl-6-nitroaniline commercially available from Aldrich, TCI, etc. was used as the starting material.

The compounds obtained in Examples 11 to 22 have the following base structures, and each corresponding substituents and $^1$H NMR data are shown in Table 2 below:

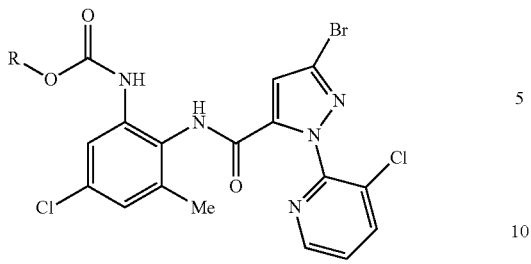

TABLE 2

| Example | R | $^1$H NMR |
|---|---|---|
| 11 | Me | $^1$H NMR(300 MHz, CDCl$_3$) δ 8.45(d, J = 4.5 Hz, 1H), 8.22(s, 1H), 7.88(d, J = 8.1 Hz, 1H), 7.44-7.37(m, 1H), 7.36(s, 1H), 7.03(s, 1H), 6.96(s, 1H), 6.88(s, 1H), 3.79(s, 3H), 2.22(s, 3H). |
| 12 | i-Bu | $^1$H NMR(300 MHz, DMSO) δ 8.44(d, J = 4.8 Hz, 1H), 8.27(dd, J = 8.0, 1.7 Hz, 1H), 7.71(s, 1H), 7.68(d, J = 2.3 Hz, 1H), 7.62(dd, J = 8.1, 4.7 Hz, 1H), 7.24(d, J = 2.0 Hz, 1H), 4.16(d, J = 6.5 Hz, 2H), 2.03-1.96(m, 1H), 0.96(d, J = 6.7 Hz, 6H). |
| 13 | n-Heptyl | $^1$H NMR(300 MHz, CDCl$_3$) δ 8.46(d, J = 4.8 Hz, 1H), 8.30(s, 1H), 7.87(d, J = 8.0 Hz, 1H), 7.38(dd, J = 8.0, 4.8 Hz, 1H), 7.32(s, 1H), 7.04(s, 1H), 6.95(s, 1H), 6.79(s, 1H), 4.17(t, J = 6.7 Hz, 2H), 2.22(s, 3H), 1.71-1.62(m, 2H), 1.41-1.22(m, 8H), 0.93-0.84(m, 3H). |
| 14 | CH$_2$=CHCH$_2$— | $^1$H NMR(300 MHz, CDCl$_3$) δ 8.46(d, J = 4.7 Hz, 1H), 8.24(s, 1H), 7.87(d, J = 8.1 Hz, 1H), 7.40-7.32(m, 2H), 7.05(s, 1H), 6.94(s, 1H), 6.89(s, 1H), 5.99-5.88(m, 0H), 5.33(dd, J = 21.7, 13.7 Hz, 2H), 4.67(d, J = 5.8 Hz, 2H), 2.23(s, 3H). |
| 15 | CH$_3$OCH$_2$CH$_2$— | $^1$H NMR(300 MHz, CDCl$_3$) δ 8.48(d, J = 4.7 Hz, 1H), 8.24(s, 1H), 7.88(d, J = 7.9 Hz, 1H), 7.38(dd, J = 8.1, 4.9 Hz, 1H), 7.34(s, 1H,) 7.05(s, 1H), 6.95(s, 1H), 6.90(s, 1H), 4.34(t, J = 4.5 Hz, 2H), 3.63(t, J = 4.4 Hz, 2H), 3.39(s, 3H), 22.22(s, 3H). |
| 16 | ClCH$_2$CH$_2$CH$_2$— | $^1$H NMR(300 MHz, CDCl$_3$) δ 8.46(d, J = 4.5 Hz, 1H), 8.18(s, 1H), 7.89(dd, J = 7.9, 1.7 Hz, 1H), 7.43-7.36(m, 2H), 7.05(s, 1H), 6.96(s, 1H), 6.90(s, 1H), 4.34(t, J = 6.0 Hz, 2H), 3.62(t, J = 6.3 Hz, 2H), 2.23(s, 3H), 2.14(p, J = 6.2 Hz, 2H). |
| 17 | BrCH$_2$CH$_2$— | $^1$H NMR(300 MHz, CDCl$_3$) δ 8.49(d, J = 4.7 Hz, 1H), 8.08(s, 1H), 7.90(d, J = 7.9 Hz, 1H), 7.41(m, 2H), 7.06(s, 1H), 7.02(s, 1H), 6.95(s, 1H), 4.49(t, J = 5.9 Hz, 2H), 3.55(t, J = 5.9 Hz, 2H), 2.23(s, 3H). |
| 18 | Cl$_3$CCH$_2$— | $^1$H NMR(300 MHz, CDCl$_3$) δ 8.49(dd, J = 4.7, 1.6 Hz, 1H), 7.96(s, 1H), 7.89(dd, J = 8.1, 1.6 Hz, 1H), 7.47(d, J = 2.2 Hz, 1H), 7.39(dd, J = 8.1, 4.7 Hz, 1H), 7.23(s, 1H), 7.10(d, J = 1.8 Hz, 1H), 6.93(s, 1H), 4.83(s, 2H), 2.25(s, 3H). |
| 19 | Cl$_3$CC(CH$_3$)$_2$— | $^1$H NMR(300 MHz, CDCl$_3$) δ 8.48(dd, J = 4.8, 1.6 Hz, 1H), 8.23(m, 1H), 7.86(dd, J = 8.0, 1.6 Hz, 1H), 7.38(dd, J = 8.0, 4.7 Hz, 1H), 7.34(s, 1H), 7.09(d, J = 2.3 Hz, 1H), 6.98(s, 1H), 6.93(s, 1H), 2.23(s, 3H), 1.96(s, 6H). |
| 20 | FCH$_2$CH$_2$— | $^1$H NMR(300 MHz, CDCl$_3$) δ 8.49(dd, J = 4.7, 1.6 Hz, 1H), 8.13(s, 1H), 7.92(dd, J = 8.0, 1.5 Hz, 1H), 7.46(d, J = 2.2 Hz, 1H), 7.41(dd, J = 8.1, 4.7 Hz, 1H), 7.08(s, 1H), 7.05(d, J = 2.2 Hz, 2H), 6.98(s, 1H), 4.74(m, 1H), 4.58(m, 1H), 4.48(m, 1H), 4.39(m, 1H), 2.25(s, 3H). |
| 21 | Et | $^1$H NMR(300 MHz, CDCl$_3$) δ 8.70(s, 1H), 8.41(dd, J = 4.7, 1.6 Hz, 1H), 7.84(dd, J = 8.1, 1.6 Hz, 1H), 7.38-7.31(m, 2H), 7.06(s, 1H), 7.03(s, 1H), 6.89(d, J = 2.3 Hz, 1H), 4.18(q, J = 7.2 Hz, 2H), 2.13(s, 3H), 1.30(t, J = 7.2 Hz, 3H). |
| 22 | n-Pr | $^1$H NMR(300 MHz, CDCl$_3$) δ 8.46(d, J = 4.6 Hz, 1H), 8.34(s, 1H), 7.87(d, J = 8.1 Hz, 1H), 7.42-7.35(m, 1H), 7.31(s, 1H), 7.03(s, 1H), 6.97(s, 1H), 6.82(s, 1H), 4.14(t, J = 6.6 Hz, 2H), 2.22(s, 3H), 1.70(q, J = 7.3 Hz, 2H), 0.97(t, J = 7.4 Hz, 3H). |

Examples 23 to 29

Steps 1 to 5 of Example 35 as described below were repeated except for using 4-chloro-2-methyl-6-nitroaniline instead of 4-amino-3-methyl-5-nitrobenzonitrile as a starting material in Step 1 and using the corresponding R$_1$-phenyl chloroformate in which R$_1$ is a substituent shown in Table 3, instead of heptyl chloroformate in Step 3, to obtain the title compounds of Examples 23 to 29. In this process, 4-chloro-2-methyl-6-nitroaniline commercially available from Aldrich, TCI, etc. was used as the starting material.

The compounds obtained in Examples 23 to 29 have the following base structures, and each corresponding substituents and $^1$H NMR data are shown in Table 3 below:

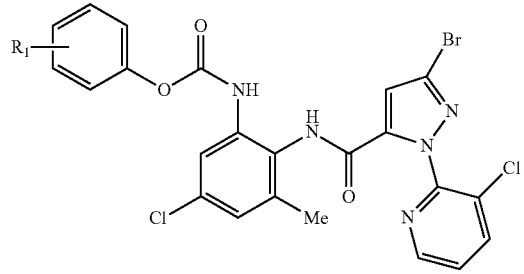

TABLE 3

| Example | $R_1$ | $^1$H NMR |
|---|---|---|
| 23 | H | $^1$H NMR(300 MHz, CDCl$_3$) δ 8.39(d, J = 4.7 Hz, 1H), 7.92(d, J = 7.9 Hz, 1H), 7.88(s, 1H), 7.50-7.42(m, 2H), 7.42-7.32(m, 3H), 7.29(s, 1H), 7.25(s, 1H), 7.20(s, 1H), 7.10(s, 1H), 2.19(s, 3H). |
| 24 | 4-OMe | $^1$H NMR(300 MHz, CDCl$_3$) δ 8.47(d, J = 4.5 Hz, 1H), 8.17(s, 1H), 7.88(d, J = 8.0 Hz, 1H), 7.44(s, 1H), 7.38(dd, J = 8.0, 4.7 Hz, 1H), 7.08-7.00(m, 3H), 6.94-6.85(m, 3H), 3.82(s, 3H), 2.25(s, 3H). |
| 25 | 4-F | $^1$H NMR(300 MHz, CDCl$_3$) δ 8.46(dd, J = 4.7, 1.6 Hz, 1H), 8.07(s, 1H), 7.88(dd, J = 8.0, 1.6 Hz, 1H), 7.48(d, J = 2.2 Hz, 1H), 7.38(dd, J = 8.0, 4.7 Hz, 1H), 7.31(s, 1H), 7.10(s, 2H), 7.08(s, 2H), 7.06(d, J = 2.2 Hz, 1H), 6.87(s, 1H), 2.25(s, 3H). |
| 26 | 4-Cl | $^1$H NMR(300 MHz, CDCl$_3$) δ 8.45(dd, J = 4.7, 1.6 Hz, 1H), 8.03(s, 1H), 7.88(dd, J = 8.0, 1.6 Hz, 1H), 7.50(d, J = 2.1 Hz, 1H), 7.38(m, 3H), 7.32(s, 1H), 7.08(m, 3H), 6.90(s, 1H), 2.26(s, 3H). |
| 27 | 2-Cl | $^1$H NMR(300 MHz, CDCl$_3$) δ 8.45(dd, J = 4.3, 1.9 Hz, 1H), 8.35(s, 1H), 7.86(dd, J = 8.0, 1.8 Hz, 1H), 7.61(s, 1H), 7.46-7.30(m, 3H), 7.25-7.16(m, 3H), 6.95(d, J = 2.5 Hz, 1H), 6.69(s, 1H), 2.19(s, 3H). |
| 28 | 4-Br | $^1$H NMR(300 MHz, CDCl$_3$) δ 8.45(dd, J = 4.7, 1.6 Hz, 1H), 8.03(s, 1H), 7.88(dd, J = 8.1, 1.6 Hz, 1H), 7.57-7.49(m, 3H), 7.38(dd, J = 8.1, 4.7 Hz, 1H), 7.33(s, 1H), 7.08(d, J = 2.2 Hz, 1H), 7.07-7.02(m, 2H), 6.89(s, 1H), 2.26(s, 3H). |
| 29 | 3-CF$_3$ | $^1$H NMR(300 MHz, CDCl$_3$) δ 8.46(d, J = 4.6 Hz, 1H), 7.96(s, 1H), 7.89(d, J = 8.1 Hz, 1H), 7.59-7.50(m, 3H), 7.44(s, 1H), 7.42-7.31(m, 3H), 7.10(s, 1H), 6.92(s, 1H), 2.27(s, 3H). |

Examples 30 to 32

Steps 1 to 5 of Example 35 as described below were repeated except for using 4-chloro-2-methyl-6-nitroaniline instead of 4-amino-3-methyl-5-nitrobenzonitrile as a starting material in Step 1 and using the corresponding R$_2$-benzyl chloroformate in which R$_2$ is a substituent shown in Table 4, instead of heptyl chloroformate in Step 3, to obtain the title compounds of Examples 30 to 32. In this process, 4-chloro-2-methyl-6-nitroaniline commercially available from Aldrich, TCI, etc. was used as the starting material.

The compounds obtained in Examples 30 to 32 have the following base structures, and each corresponding substituents and $^1$H NMR data are shown in Table 4 below:

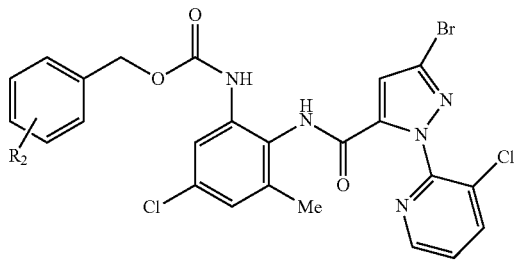

Example 35

Heptyl (2-(3-bromo-1-(3-chloropyridin-2-yl)-1H-pyrazole-5-carboxamido)-5-cyano-3-methylphenyl) carbamate

Step 1. Di-t-butyl (4-cyano-2-methyl-6-nitrophenyl)imidodicarbonate

4-Amino-3-methyl-5-nitrobenzonitrile (10.6 g, 60 mmol) was added with THF (0.5 M, 120 mL) and dissolved. Di-t-butyl dicarbonate (28.8 g, 2.2 eq, 132 mmol) and 4-dimethylaminopyridine (1.47 g, 0.2 eq, 12 mmol) were added to the solution thus obtained, and the mixture was heated under reflux for 1 hour. Upon completion of the reaction, the solvent was removed under reduced pressure, to which distilled water was added. The resulting product was extracted with ethyl acetate, and the organic layer was dried over MgSO$_4$ and concentrated under reduced pressure. Subsequently, the residue was purified by silica gel column chromatography (EA: Hex=1:9→1:4) to obtain the title compound in an ivory solid (21.6 g, yield: 95%).

In this step, the starting material, 4-amino-3-methyl-5-nitrobenzonitrile, was synthesized by using the method disclosed in WO 2007/56155 A1.

$^1$H NMR (300 MHz, CDCl$_3$) δ 8.15 (s, 1H), 7.80 (s, 1H), 2.37 (s, 3H), 1.41 (s, 18H).

TABLE 4

| Example | $R_2$ | $^1$H NMR |
|---|---|---|
| 30 | H | $^1$H NMR(300 MHz, CDCl$_3$) δ 8.33(dd, J = 4.8, 1.6 Hz, 1H), 8.17(s, 1H), 7.75(dd, J = 8.0, 1.6 Hz, 1H), 7.44-7.38(m, 5H), 7.27(s, 1H), 7.28-7.25(m, 1H), 7.05(d, J = 2.3 Hz, 1H), 6.94(s, 1H), 6.88(s, 1H), 5.19(s, 2H), 2.23(s, 3H). |
| 31 | 4-NO$_2$ | $^1$H NMR(300 MHz, CDCl$_3$) δ 8.40(dd, J = 4.7, 1.6 Hz, 1H), 8.29-8.23(m, 2H), 8.06(s, 1H), 7.85(dd, J = 8.1, 1.6 Hz, 1H), 7.53(d, J = 8.8 Hz, 2H), 7.43(d, J = 2.2 Hz, 1H), 7.35(dd, J = 8.0, 4.7 Hz, 1H), 7.07(d, J = 2.0 Hz, 2H), 6.89(s, 1H), 5.28(s, 2H), 2.23(s, 3H). |
| 32 | 2-Cl | $^1$H NMR(300 MHz, CDCl$_3$) δ 8.38(dd, J = 4.7, 1.6 Hz, 1H), 8.17(s, 1H), 7.79(dd, J = 8.0, 1.6 Hz, 1H), 7.44-7.37(m, 3H), 7.34-7.26(m, 3H), 7.05(dd, J = 2.4, 0.9 Hz, 1H), 6.99(s, 1H), 6.88(s, 1H), 5.35(s, 2H), 2.22(s, 3H). |

Step 2. Di-t-butyl (2-amino-4-cyano-6-methylphenyl)imidodicarbonate

Di-t-butyl (4-cyano-2-methyl-6-nitrophenyl)imidodicarbonate obtained in Step 1 (3.77 g, 10 mmol) was dissolved in THF (0.2 M, 50 mL), and a solution prepared by dissolving sodium hydrosulfite (15.7 g, 9 eq, 90 mmol) and sodium bicarbonate (7.56 g, 90 mmol) in $H_2O$ (0.1 M, 100 mL) was added thereto. Subsequently, MeOH (17 mL) was added to the mixture, which was then stirred at room temperature for 1 hour. Upon completion of the reaction, THF and MeOH were removed under reduced pressure, and the residue was added with brine and extracted with ethyl acetate. The organic layer thus obtained was dried over $MgSO_4$ and concentrated under reduced pressure. Then, the residue was purified by silica gel column chromatography (EA:Hex=1:2) to obtain the title compound in a white solid (2.90 g, yield: 83%).

$^1$H NMR (300 MHz, $CDCl_3$) δ 6.89 (s, 1H), 6.85 (s, 1H), 3.89 (s, 2H), 2.15 (s, 3H), 1.41 (s, 18H).

Step 3. t-Butyl t-butoxycarbonyl(4-cyano-2-(((heptyloxy)carbonyl)amino)-6-methylphenyl)carbamate Di-t-butyl (2-amino-4-cyano-6-methylphenyl)imidodicarbonate (104 mg, 0.3 mmol) obtained in Step 2 was added with pyridine (0.24 mL, 3 mmol, 10 eq) and heptyl chloroformate (0.11 mL, 0.6 mmol, 2 eq), and the mixture thus obtained was stirred at room temperature for 10 minutes, followed by further stirring at 80° C. for 2 hours. Upon completion of the reaction, the resulting product was added with distilled water, and extracted with ethyl acetate. The organic layer thus obtained was dried over $MgSO_4$, and concentrated under reduced pressure. Subsequently, the residue was purified by silica gel column chromatography (EA:Hex=1:9) to obtain the title compound in a colorless liquid (146 mg, yield: 99%).

$^1$H NMR (300 MHz, $CDCl_3$) δ 8.31 (s, 1H), 7.22 (s, 1H), 6.74 (s, 1H), 4.17 (t, J=6.7 Hz, 2H), 2.21 (s, 3H), 1.69-1.65 (m, 2H), 1.38 (s, 18H), 1.32-1.21 (m, 8H), 0.89 (t, J=5.9 Hz, 3H).

Step 4. Heptyl (2-amino-5-cyano-3-methylphenyl)carbamate t-Butyl t-butoxycarbonyl(4-cyano-2-(((heptyloxy)carbonyl)amino)-6-methylphenyl)carbamate (416 mg, 0.85 mmol) obtained in Step 3 was dissolved in $CH_2Cl_2$ (3.0 mL), added with TFA (1.95 mL, 30 eq, 25.5 mmol) and stirred at room temperature for 2 hours. Subsequently, the mixture thus obtained was added with sat. $NaHCO_3$ and extracted with $CH_2Cl_2$. The organic layer thus obtained was dried over $MgSO_4$ and concentrated under reduced pressure to obtain the title compound in a white solid (245 mg, yield: 99%).

$^1$H NMR (300 MHz, $CDCl_3$) δ 7.41 (s, 1H), 7.24 (s, 1H), 6.06 (s, 1H), 4.24 (brs, 2H), 4.17 (t, J=6.7 Hz, 2H), 2.20 (s, 3H), 1.74-1.60 (m, 2H), 1.40-1.23 (m, 8H), 0.89 (t, J=6.4 Hz, 3H).

Step 5. Heptyl (2-(3-bromo-1-(3-chloropyridin-2-yl)-1H-pyrazole-5-carboxamido)-5-cyano-3-methylphenyl)carbamate The procedure of Step 3 in Example 1 was repeated except for using heptyl (2-amino-5-cyano-3-methylphenyl)carbamate obtained in Step 4 instead of methyl (2-amino-3,5-dichlorophenyl)carbamate and using trifluoromethylsulfonyl chloride instead of methylsulfonyl chloride to obtain the title compound in a yellowish solid (yield: 65%).

$^1$H NMR (300 MHz, $CDCl_3$) δ 8.60 (s, 1H), 8.47 (d, J=4.6 Hz, 1H), 7.89 (d, J=8.1 Hz, 1H), 7.61 (s, 1H), 7.40 (dd, J=7.9, 4.7 Hz, 1H), 7.35 (s, 1H), 6.92 (s, 1H), 6.97 (s, 1H), 4.19 (t, J=6.8 Hz, 2H), 2.29 (s, 3H), 1.74-1.61 (m, 2H), 1.41-1.21 (m, 8H), 0.93-0.82 (m, 3H).

Examples 33, 34, and 36 to 39

Steps 1 to 5 of Example 35 as described above were repeated except for using the corresponding R-chloroformate in which R is a substituent shown in Table 5, instead of heptyl chloroformate in Step 3, to obtain the title compounds of Examples 33, 34 and 36 to 39.

The compounds obtained in Examples 30 to 32 have the following base structures, and each corresponding substituents and $^1$H NMR data are shown in Table 5 below:

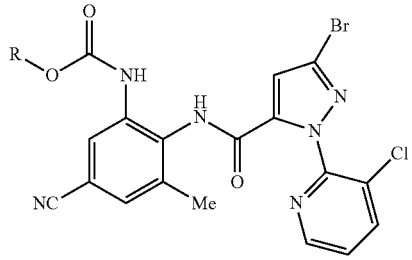

TABLE 5

| Example | R | $^1$H NMR |
|---|---|---|
| 33 | Me | $^1$H NMR(300 MHz, $CDCl_3$) δ 8.45(d, J = 4.5 Hz, 2H), 7.90(d, J = 7.9 Hz, 1H), 7.67(s, 1H), 7.41(dd, J = 8.1, 4.7 Hz, 1H), 7.34(d, J = 1.8 Hz, 1H), 7.01(s, 1H), 6.97(s, 1H), 3.82(s, 3H), 2.29(s, 3H). |
| 34 | i-Bu | $^1$H NMR(300 MHz, $CDCl_3$) δ 8.62(s, 1H), 8.46(d, J = 5.0 Hz, 1H), 7.89(d, J = 8.2 Hz, 1H), 7.60(s, 1H), 7.40(dd, J = 8.0, 4.7 Hz, 1H), 7.34(s, 1H), 6.96(d, J = 4.3 Hz, 2H), 3.99(d, J = 6.6 Hz, 2H), 2.29(s, 3H), 2.01-1.93(m, 1H), 0.96(d, J = 6.6 Hz, 6H). |
| 35 | n-Heptyl | $^1$H NMR(300 MHz, $CDCl_3$) δ 8.60(s, 1H), 8.47(d, J = 4.6 Hz, 1H), 7.89(d, n-Hepty1 = , J 8.1 Hz, 1H), 7.61(s, 1H), 7.40(dd, J = 7.9, 4.7 Hz, 1H), 7.35(s, 1H), 6.92(s, 1H), 6.97(s, 1H), 4.19(t, J = 6.8 Hz, 2H), 2.29(s, 3H), 1.74-1.61 (m, 2H), 1.41-1.21(m, 8H), 0.93-0.82(m, 3H). |
| 36 | $CH_2=CHCH_2-$ | $^1$H NMR(300 MHz, $CDCl_3$) δ 8.50(s, 1H), 8.46(d, J = 4.8 Hz, 1H), 7.90(d, J = 7.8 Hz, 1H), 7.65(s, 1H), 7.40(dd, J = 7.9, 4.7 Hz, 1H), 7.36(s, 1H), 7.02(s, 1H), 6.95(s, 1H), 6.01-5.89(m, 1H), 5.38(d, J = 17.1 Hz, 1H), 5.32(d, J = 10.4 Hz, 1H), 4.70(d, J = 5.8 Hz, 2H), 2.30(s, 3H). |

TABLE 5-continued

| Example | R | $^1$H NMR |
|---|---|---|
| 37 | $CH_3OCH_2CH_2$— | $^1$H NMR(300 MHz, CDCl$_3$) δ 8.49(d, J = 4.2 Hz, 2H), 7.90(d, J = 8.1 Hz, 1H), 7.66(s, 1H), 7.40(dd, J = 7.9, 4.7 Hz, 1H), 7.35(s, 1H), 7.03(s, 1H), 6.97(s, 1H), 4.37(t, J = 4.4 Hz, 2H), 3.64(t, J = 4.4 Hz, 2H), 3.40(s, 3H), 2.29(s, 3H). |
| 38 | $ClCH_2CH_2CH_2$— | $^1$H NMR(300 MHz, CDCl$_3$) δ 8.47(d, J = 4.7 Hz, 1H), 8.41(s, 1H), 7.91(d, J = 8.7 Hz, 1H), 7.70(s, 1H), 7.44-7.39(m, 1H), 7.36(s, 1H), 7.02(s, 1H), 6.97(s, 1H), 4.38(t, J = 6.0 Hz, 2H), 3.63(t, J = 6.3 Hz, 2H), 2.31(s, 3H), 2.15(t, J = 6.0 Hz, 2H). |
| 39 | $BrCH_2CH_2$— | $^1$H NMR(300 MHz, CDCl$_3$) δ 8.49(d, J = 3.5 Hz, 1H), 8.29(s, 1H), 7.92(d, J = 7.9 Hz, 1H), 7.76(s, 1H), 7.45-7.38(m, 1H), 7.36(s, 1H), 7.16(s, 1H), 6.97(s, 1H), 4.52(t, J = 5.9 Hz, 2H), 3.56(t, J = 5.9 Hz, 2H), 2.31(s, 3H). |

Examples 40 to 47

Steps 1 to 5 of Example 35 as described above were repeated except for using 4-bromo-2-Y-6-nitroaniline in which Y is a substituent shown in Table 6, instead of 4-amino-3-methyl-5-nitrobenzonitrile in Step 1, and using the corresponding R-chloroformate in which R is a substituent shown in Table 6, instead of heptyl chloroformate in Step 3, to obtain the title compounds of Examples 40 to 47. In this process, 4-bromo-2-Y-6-nitroaniline commercially available from Aldrich, TCI, etc. was used as the starting material.

The compounds obtained in Examples 40 to 47 have the following base structures, and each corresponding substituents and $^1$H NMR data are shown in Table 6 below:

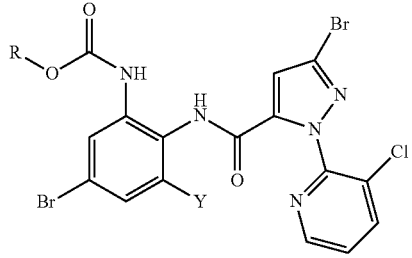

TABLE 6

| Example | R | Y | $^1$H NMR |
|---|---|---|---|
| 40 | Me | Br | $^1$H NMR(300 MHz, CDCl$_3$) δ 8.48(d, J = 4.7 Hz, 1H), 8.01-7.88(m, 3H), 7.55(s, 1H), 7.45-7.39(m, 1H), 7.23(s, 1H) 7.03(s, 1H), 3.77(s, 3H). |
| 41 | i-Bu | Br | $^1$H NMR(300 MHz, CDCl$_3$) δ 8.48(d, J = 4.5 Hz, 1H), 8.18(d, J = 22.1 Hz, 1H), 7.96-7.85(m, 2H), 7.51(d, J = 2.2 Hz, 1H), 7.41(dd, J = 8.0, 4.7 Hz, 1H), 7.23(s, 1H), 7.07(d, J = 5.4 Hz, 1H), 3.92(d, J = 6.8 Hz, 2H), 1.96(dt, J = 13.4, 6.7 Hz, 1H), 0.95(d, J = 6.7 Hz, 6H). |
| 42 | n-Heptyl | Br | $^1$H NMR(300 MHz, CDCl$_3$) δ 8.46(d, J = 4.6 Hz, 1H), 8.35(s, 1H), 7.87(d, J = 9.8 Hz, 2H), 7.47(s, 1H), 7.38(dd, J = 7.7, 4.6 Hz, 1H), 7.21(s, 1H), 7.08(s, 1H), 4.10(t, J = 6.8 Hz, 2H), 1.68-1.60(m, 2H), 1.35-1.25(m, 8H), 0.88(t, J = 6.5 Hz, 3H). |
| 43 | $CH_2$=$CHCH_2$— | Br | $^1$H NMR(300 MHz, CDCl$_3$) δ 8.52(d, J = 4.5 Hz, 1H), 8.01(s, 1H), 7.97-7.89(m, 3H), 7.56(s, 1H), 7.43(dd, J = 8.2, 4.6 Hz, 1H), 7.36(s, 1H), 7.04(s, 1H), 4.46(t, J = 5.9 Hz, 2H), 3.55(t, J = 6.0 Hz, 2H). |
| 44 | $CH_3OCH_2CH_2$— | Br | $^1$H NMR(300 MHz, CDCl$_3$) δ 8.53(d, J = 4.5 Hz, 1H), 7.95(t, J = 11.0 Hz, 3H), 7.55(s, 1H), 7.46-7.35(m, 1H), 7.23(s, 1H), 7.03(s, 1H), 4.31(t, J = 4.4 Hz, 2H), 3.63(t, J = 4.4 Hz, 2H), 3.40(s, 3H). |
| 45 | $ClCH_2CH_2CH_2$— | Br | $^1$H NMR(300 MHz, CDCl$_3$) δ 8.50(d, J = 4.9 Hz, 1H), 8.00(s, 1H), 7.93(d, J = 6.9 Hz, 2H), 7.55(s, 1H), 7.44(dd, J = 8.0, 4.7 Hz, 1H), 7.29(s, 1H), 7.04(s, 1H), 4.32(t, J = 6.0 Hz, 2H), 3.62(t, J = 6.3 Hz, 2H), 2.13(dt, J = 12.6, 5.9 Hz, 2H). |
| 46 | $BrCH_2CH_2$— | Br | $^1$H NMR(300 MHz, CDCl$_3$) δ 8.52(d, J = 4.5 Hz, 1H), 8.01(s, 1H), 7.97-7.89(m, 3H), 7.56(s, 1H), 7.43(dd, J = 8.2, 4.6 Hz, 1H), 7.36(s, 1H), 7.04(s, 1H), 4.46(t, J = 5.9 Hz, 2H), 3.55(t, J = 6.0 Hz, 2H). |
| 47 | i-Bu | Me | $^1$H NMR(300 MHz, CDCl$_3$) δ 8.34(dd, J = 4.7, 1.8 Hz, 1H), 7.96(d, J = 2.2 Hz, 1H), 7.89(dd, J = 8.1, 1.7 Hz, 1H), 7.34(dd, J = 8.0, 4.6 Hz, 1H), 7.21(s, 1H), 7.16(s, 1H), 4.22(d, J = 6.6 Hz, 2H), 2.14-2.08(m, 1H), 1.03(d, J = 6.7 Hz, 6H). |

Examples 48 to 53

Steps 1 to 5 of Example 35 as described above were repeated except for using the corresponding 4-trifluoromethyl-2-Y-6-nitroaniline in which Y is a substituent shown in Table 7, instead of 4-amino-3-methyl-5-nitrobenzonitrile in Step 1, and using the corresponding R-chloroformate in which R is a substituent shown in Table 7, instead of heptyl chloroformate in Step 3, to obtain the title compounds of Examples 48 to 53. In this process, 4-trifluoromethyl-2-Y-6-nitroaniline commercially available from Aldrich, TCI, etc. was used as the starting material.

The compounds obtained in Examples 48 to 53 have the following base structure, and each corresponding substituents and $^1$H NMR data are shown in Table 7 below:

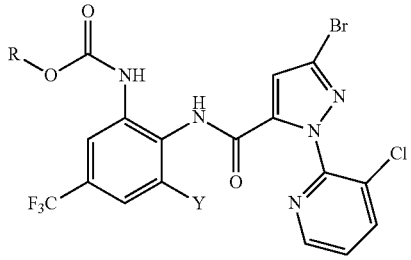

TABLE 7

| Example | R | Y | $^1$H NMR |
|---|---|---|---|
| 48 | Me | Cl | $^1$H NMR(300 MHz, CDCl$_3$) δ 8.49(dd, J = 4.7, 1.7 Hz, 1H), 8.27(s, 1H), 8.06(s, 1H), 7.94(dd, J = 8.1, 1.7 Hz, 1H), 7.49(s, 1H), 7.44(dd, J = 8.0, 4.6 Hz, 1H), 7.35(s, 1H), 7.05(s, 1H), 3.79(s, 3H) |
| 49 | i-Bu | Cl | $^1$H NMR(300 MHz, CDCl$_3$) δ 8.52(dd, J = 4.7, 1.6 Hz, 1H), 8.27(s, 1H), 8.06(s, 1H), 7.94(dd, J = 8.1, 1.6 Hz, 1H), 7.50(d, J = 1.7 Hz, 2H), 7.44(dd, J = 8.1, 4.7 Hz, 1H), 7.33(s, 1H), 7.07(s, 1H), 3.98(d, J = 6.7 Hz, 2H), 1.99(m, 1H), 0.98(d, J = 6.7 Hz, 6H). |
| 50 | n-Heptyl | Cl | $^1$H NMR(300 MHz, CDCl$_3$) δ 8.52(dd, J = 4.8, 1.5 Hz, 1H), 8.26(s, 1H), 8.07(s, 1H), 7.94(dd, J = 8.1, 1.6 Hz, 1H), 7.50(d, J = 1.9 Hz, 1H), 7.44(dd, J = 8.1, 4.7 Hz, 1H), 7.07(s, 1H), 4.18(t, J = 6.8 Hz, 2H), 1.69(t, J = 6.8 Hz, 2H), 1.40-1.28(m, 8H), 0.94-0.88(m, 3H). |
| 51 | Me | Br | $^1$H NMR(300 MHz, CDCl$_3$) δ 8.50-8.42(m, 2H), 8.07(s, 1H), 7.90(d, J = 8.0 Hz, 1H), 7.58(s, 1H), 7.43-7.36(m, 2H), 7.06(s, 1H), 3.75(s, 3H) |
| 52 | i-Bu | Br | $^1$H NMR(300 MHz, CDCl$_3$) δ 8.52(dd, J = 4.7, 1.6 Hz, 1H), 8.16(s, 1H), 8.12(s, 1H), 7.94(dd, J = 8.0, 1.5 Hz, 1H), 7.66(d, J = 1.9 Hz, 1H), 7.44(dd, J = 8.1, 4.7 Hz, 1H), 7.32(s, 1H), 7.08(s, 1H), 3.97(d, J = 6.7 Hz, 2H), 2.05-1.93(m, 1H), 0.98(d, J = 6.7 Hz, 6H). |
| 53 | n-Heptyl | Br | $^1$H NMR(300 MHz, CDCl$_3$) δ 8.52(dd, J = 4.7, 1.6 Hz, 1H), 8.13(s, 2H), 7.94(dd, J = 8.0, 1.6 Hz, 1H), 7.66(d, J = 1.8 Hz, 1H), 7.44(dd, J = 8.0, 4.7 Hz, 1H), 7.08(s, 1H), 4.18(t, J = 6.8 Hz, 2H), 1.68(d, J = 7.3 Hz, 2H), 1.31(t, J = 11.6 Hz, 8H), 0.96-0.86(m, 3H). |

Example 54

Methyl (2-(3-bromo-1-(3-chloropyridin-2-yl)-1H-pyrazole-5-carboxamido)-3-methylphenyl)carbamate Step 1. 3-Bromo-1-(3-chloropyridin-2-yl)-N-(2-methyl-6-nitrophenyl)-1H-pyrazole-5-carboxamide

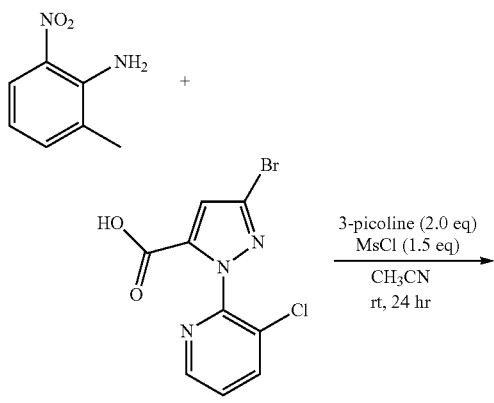

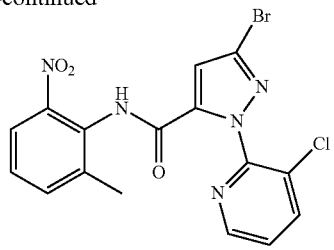

2-Methyl-6-nitroaniline (540 mg, 3.54 mmol), 3-bromo-1-(3-chloropyridin-2-yl)-1H-pyrazole-5-carboxylic acid (1 g, 3.54 mmol), CH$_3$CN (0.3 M, 11.8 mL) and 3-picoline (0.69 mL, 7.08 mmol, 2.0 eq) were introduced to a 50 mL round flask and subjected to a reaction at room temperature. After 10 minutes, the reaction mixture thus obtained was added with methylsulfonylchloride (0.41 mL, 5.31 mmol, 1.5 eq.), subjected to a reaction at 30° C. for 24 hours, and followed by a further reaction at 40° C. for 24 hours. Upon completion of the reaction, CH$_3$CN was removed from the reaction mixture under reduced pressure, and the residue was extracted with 1 M HCl (20 mL) and ethyl acetate (20 mL), and, then, extracted with NaHCO$_3$ (20 mL) and ethyl acetate (20 mL), washed with brine (20 mL). The organic layer thus obtained was dried over MgSO$_4$ and concentrated under reduced pressure. Subsequently, the residue was purified by silica gel column chromatography (MC:EA=9:1) to obtain the title compound (1.27 g, yield: 82%).

In this step, the starting material, 3-bromo-1-(3-chloropyridin-2-yl)-1H-pyrazole-5-carboxylic acid, was prepared by the method disclosed in Lahm, George P. et al., Rynaxypyr: a new insecticidal anthranilic diamide that acts as a potent and selective ryanodine receptor activator, *Bioorganic and Medicinal Chemistry Letters*, 2007, vol. 17, #22, pp. 6274-6279 or WO 2003/106427 A2 (E.I. DUPONT DE NEMOURS AND COMPANY et al.)

$^1$H NMR (300 MHz, CDCl$_3$) δ 9.18 (s, 1H), 8.47 (d, J=4.6 Hz, 1H), 7.89 (t, J=7.7 Hz, 2H), 7.52 (d, J=8.0 Hz, 1H), 7.38 (q, J=4.3 Hz, 1H), 7.32 (t, J=8.2 Hz, 1H), 7.02 (s, 1H), 2.29 (s, 3H) .

Step 2. N-(2-amino-6-methylphenyl)-3-bromo-1-(3-chloropyridin-2-yl)-1H-pyrazole-5-carboxamide

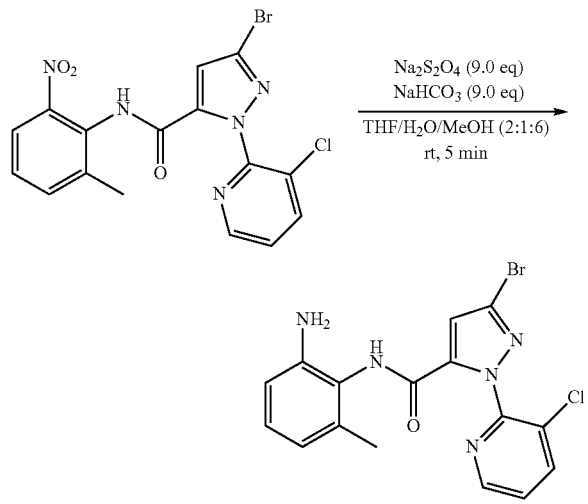

3-Bromo-1-(3-chloropyridin-2-yl)-N-(2-methyl-6-nitrophenyl)-1H-pyrazole-5-carboxamide prepared in Step 1 (1.27 g, 2.91 mmol), THF (0.2 M, 14.6 mL) and $Na_2S_2O_4$ (5.37 g, 26.2 mmol, 9.0 eq) were added to a 100 mL round flask and stirred. In a separate flask, $NaHCO_3$ (2.20 g, 26.2 mmol, 9.0 eq) was dissolved in $H_2O$ (0.1 M, 29.1 mL) and slowly added to the reaction solution. MeOH (0.6 M, 4.9 mL) was added to the reaction solution, subjected to a reaction at room temperature for 5 minutes, and the solvent was removed therefrom under reduced pressure upon completion of the reaction. The residue was extracted with ethyl acetate (20 mL x 2) and brine (20 mL x 2), and the organic layer thus obtained was dried over $MgSO_4$ and concentrated under reduced pressure. Upon completion of removing the solvent, the residue was dissolved in a small quantity of ethyl acetate, wetted with ethyl acetate/hexane (1:1) and then filtered. The solvent was removed under reduced pressure to obtain the title compound.

$^1$H NMR (300 MHz, $CDCl_3$) δ 8.45 (d, J=4.4 Hz, 1H), 7.88 (d, J=8.3 Hz, 2H), 7.38 (q, J=4.4 Hz, 3H), 7.00 (t, J=7.8 Hz, 1H), 6.93 (s, 1H), 6.63 (t, J=9.0 Hz, 3H), 2.19 (s, 3H)

Step 3. Methyl (2-(3-bromo-1-(3-chloropyridin-2-yl)-1H-pyrazole-5-carboxamido)-3-methylphenyl)carbamate

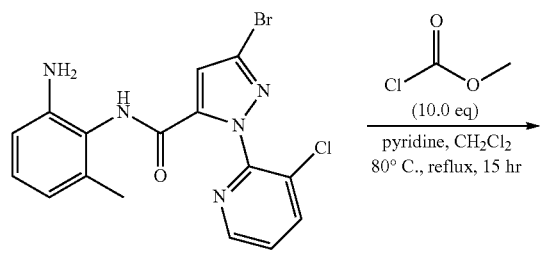

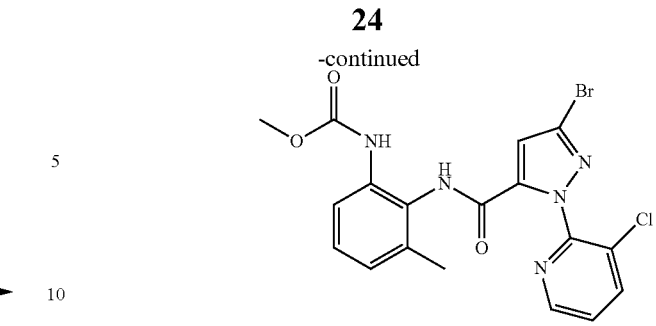

N-(2-amino-6-methylphenyl)-3-bromo-1-(3-chloropyridin-2-yl)-1H-pyrazole-5-carboxamide prepared in Step 2 (1.18 g, 2.91 mmol), $CH_2Cl_2$ (2 M, 1.46 mL) and pyridine (1 M, 2.91 mL) were introduced to a 50 mL round flask. The mixture thus obtained was cooled down to 0° C., added with methyl chloroformate (2.25 mL, 29.1 mmol, 10.0 eq), and refluxed at 80° C. for 15 hours. Upon completion of the reaction, the solvent was removed under reduced pressure. The residue was extracted with 1 M HCl (20 mL) and ethyl acetate (20 mL x 2), washed with brine (20 mL). The organic layer thus obtained was dried over $MgSO_4$ and concentrated under reduced pressure. Subsequently, the residue was purified by silica gel column chromatography (EA:Hex=2:3→EA:Hex=1:1) to obtain the title compound (426.7 mg, yield: 32%).

$^1$H NMR (300 MHz, $CDCl_3$) δ 8.46 (d, J=4.7 Hz, 1H), 7.87 (d, J=8.8 Hz, 1H), 7.38 (q, J=4.3 Hz, 1H), 7.18 (q, J=7.7 Hz, 2H), 7.06 (d, J=7.2 Hz, 1H), 6.94 (s, 1H), 6.83 (s, 1H), 3.79 (s, 3H), 2.23 (s, 3H).

Example 55

Methyl (2-(3-bromo-1-(3-chloropyridin-2-yl)-1H-pyrazole-5-carboxamido)-3-methyl-5-nitrophenyl)carbamate

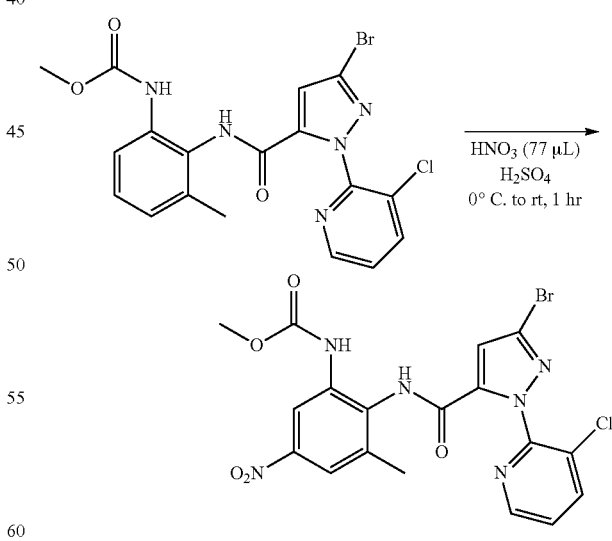

Methyl (2-(3-bromo-1-(3-chloropyridin-2-yl)-1H-pyrazole-5-carboxamido)-3-methylphenyl)carbamate prepared in Example 54 (100 mg, 0.22 mmol) was introduced in a V-shaped vial, and the vial was placed in an ice bath. $H_2SO_4$ (0.5 mL) was added to the vial at 0° C. and subjected to a reaction until the solid disappeared. After the solid completely disappeared, HNO₃ (77 μL, 1.29 mmol, 6.0 eq) was added to the solution dropwise. The vial was removed from the ice bath 10 minutes after the initiation of the reaction, and the reaction mixture was allowed to react at room temperature for 1 hour. Upon completion of the reaction, 15 mL of ice was placed in a 50 mL flask, and the reaction mixture was added thereto. The reaction mixture was washed with water several times and filtered. The residue was extracted with ether and H₂O, dried over MgSO₄ and concentrated under reduced pressure. Subsequently, the residue was purified by silica gel column chromatography (EA:Hex=1:1) to obtain the title compound in a white solid (95 mg, yield: 85%).

¹H NMR (300 MHz, CDCl₃) δ 9.31 (s, 1H), 9.14 (s, 1H), 8.67 (s, 1H), 8.47 (d, J=5.3 Hz, 1H), 7.88 (d, J=9.5 Hz, 1H), 7.41 (q, J=4.2 Hz, 2H), 6.98 (s, 1H), 3.91 (s, 3H), 2.52 (s, 3H)

The compounds obtained in Examples 54 and 55 have the following base structure, and each corresponding substituents and ¹H NMR data are shown in Table 8 below:

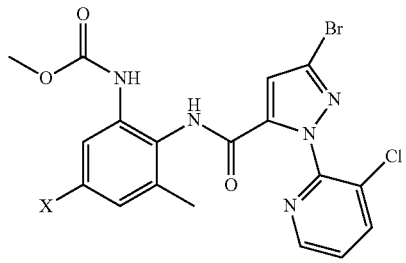

TABLE 8

| Example | X | ¹H NMR |
|---|---|---|
| 54 | H | ¹H NMR(300 MHz, CDCl₃) δ 8.46(d, J = 4.7 Hz, 1H), 7.87(d, J = 8.8 Hz, 1H), 7.38(q, J = 4.3 Hz, 1H), 7.18(q, J = 7.7 Hz, 2H), 7.06(d, J = 7.2 Hz, 1H), 6.94(s, 1H), 6.83(s, 1H), 3.79(s, 3H), 2.23(s, 3H) |
| 55 | Nitro | ¹H NMR(300 MHz, CDCl₃) δ 9.31(s, 1H), 9.14(s, 1H), 8.67(s, 1H), 8.47(d, J = 5.3 Hz, 1H), 7.88(d, J = 9.5 Hz, 1H), 7.41(q, J = 4.2 Hz, 2H), 6.98(s, 1H), 3.91(s, 3H), 2.52(s, 3H) |

Examples 56 to 64

Steps 1 to 5 of Example 35 as described above were repeated except for using the corresponding R-chloroformate in which R is a substituent shown in Table 9, instead of heptyl chloroformate in Step 3, and using the corresponding carboxylic acid which has substituents Z and V as shown in Table 9, instead of 3-bromo-1-(3-chloropyridin-2-yl)-1H-pyrazole-5-carboxylic acid in Step 5, to obtain the title compounds of Examples 56 to 64. In this process, the carboxylic acids used in Step 5 were prepared by the methods disclosed in Feng, Q. et. al. *J. Agric. Food. Chem.* 2010, 58, pp. 12327-12336; *Chin. J. Chem.* 2010, 28, pp. 1757-1760; *Chin. J. Chem.* 2012, 30, pp. 1748-1758; US 2010/273830 A1; *J. Agric. Food Chem.* 2012, 60, pp. 7565-7572; and WO 2008/73825 A1.

The compounds obtained in Examples 56 to 64 have the following base structure, and each corresponding substituents and ¹H NMR data are shown in Table 9 below:

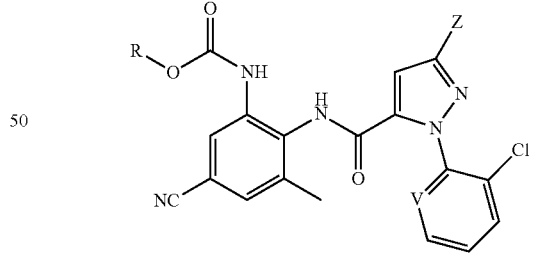

TABLE 9

| Example | R | Z | V | ¹H NMR |
|---|---|---|---|---|
| 56 | Me | Cl | N | ¹H NMR(300 MHz, CDCl₃) δ 8.57(s, 1H), 8.44(dd, J = 1.6, 4.7 Hz, 1H)7.90(dd, J = 1.6, 8.0 Hz, 1H) 7.66(s, 1H), 7.40(q, J = 4.3 Hz, 1H) 7.31(s, 1H), 7.09(s, 1H), 6.90(s, 1H), 3.81(s, 3H), 2.28(s, 3H) |
| 57 | Me | CN | N | ¹H NMR(300 MHz, CDCl₃) δ 8.88(s, 1H), 8.48(dd, J = 1.5, 4.7 Hz, 1H)7.95(dd, J = 1.6, 8.0 Hz, 1H) 7.57(s, 1H), 7.48(q, J = 4.3 Hz, 1H) 7.34(s, 1H), 7.33(s, 1H), 7.03(s, 1H), 3.83(s, 3H), 2.28(s, 3H) |

TABLE 9-continued

| Example | R | Z | V | $^1$H NMR |
|---|---|---|---|---|
| 58 | Me | MeO— | N | $^1$H NMR(300 MHz, CDCl$_3$) δ 8.44(dd, J = 1.6, 4.7 Hz, 1H) 8.37(s, 1H), 7.87(dd, J = 1.6, 8.0 Hz, 1H)7.75(s, 1H), 7.35(q, J = 4.3 Hz, 1H) 7.32(s, 1H), 7.18(s, 1H), 6.38(s, 1H), 4.00(s, 3H), 3.79(s, 3H), 2.28(s, 3H) |
| 59 | Me | CH$_3$NHC(=O)— | N | $^1$H NMR(300 MHz, CDCl$_3$) δ 9.97(s, 1H), 8.51(dd, J = 1.5, 4.7 Hz, 1H), 8.29(s, 1H), 8.12(s, 1H), 7.91(dd, J = 1.6, 8.1 Hz, 1H), 7.45(q, J = 4.3 Hz, 1H), 7.28(s, 1H), 7.22(s, 1H), 7.13(d, J = 5.3 Hz, 1H), 3.76(s, 3H), 2.54 (d, J = 5.0 Hz, 4.7 Hz, 3H), 2.36(s, 3H) |
| 60 | Me | CF$_3$CH$_2$O— | N | $^1$H NMR(300 MHz, CDCl$_3$) δ 8.47 s, 1H), 8.44 dd, J = 1.6, 1H), 7.89(dd, J = 1.6, 8.0 Hz, 1H), 7.68(s, 1H), 7.38(q, J = 4.2 Hz, 1H), 7.29(s, 1H), 7.10(s, 1H), 6.48(s, 1H), 4.69(q, J = 8.3 Hz, 2H), 3.80(s, 3H), 2.27(s, 3H) |
| 61 | Me | CF$_3$— | N | $^1$H NMR(300 MHz, CDCl$_3$) δ 8.77(s, 1H), 8.48(dd, J = 1.6, 4.7 Hz, 1H)7.93(dd, J = 1.6, 8.0 Hz, 1H) 7.60(s, 1H), 7.45(q, J = 4.3 Hz, 1H), 7.33(s, 1H), 7.26(s, 1H), 7.01(s, 1H), 3.81(s, 3H), 2.30(s, 3H) |
| 62 | Me | CF$_3$— | C | $^1$H NMR(300 MHz, CDCl$_3$) δ 8.60(s, 1H), 7.55-7.53(m, 2H), 7.46-7.42(m, 3H), 7.30(s, 1H), 7.26(s, 1H), 6.99(s, 1H), 3.77(s, 3H), 2.28(s, 3H) |
| 63 | Et | Br | N | $^1$H NMR(300 MHz, CDCl$_3$) δ 8.62(s, 1H), 8.46(d, J = 4.1 Hz, 1H), 7.89(d, J = 7.6 Hz, 1H), 7.63(s, 1H), 7.40(dd, J = 8.1, 4.7 Hz, 1H), 7.32(s, 1H), 6.99(s, 1H), 6.97(s, 1H), 4.26(q, J = 7.0 Hz, 2H), 2.29 (s, 3H), 1.33(t, J = 7.1 Hz, 3H). |
| 64 | ClCH$_2$CH$_2$— | Br | N | $^1$H NMR(300 MHz, CDCl$_3$) δ 8.49(d, J = 4.8 Hz, 1H), 8.35(s, 1H), 7.92(d, J = 8.1 Hz, 1H), 7.75(s, 1H), 7.42(dd, J = 8.3, 4.8 Hz, 1H), 7.35(s, 1H), 7.19(s, 1H), 6.96(s, 1H), 4.45(t, J = 5.7 Hz, 2H), 3.74(t, J = 5.4 Hz, 2H), 2.30(s, 3H). |

The compounds prepared in the above Examples were bioassayed to measure insecticidal activities against diamondback moth and tobacco cutworm moth, acute toxicity against honeybee and Log P values, as described below.

Experimental Example 1

Insecticidal Activities Against Diamondback Moth (*Plutella xylostella*) Measured by Leaf-Dip Method In this test, larvae descended from diamondback moths (*Plutella xylostella*), which had been collected in 2000 near Gyeongju area and reared in the laboratory, were used. Cabbage leaves (Dia) were cut into fragments having a diameter of 5.8 cm, immersed in a 5% acetone solution in which the test compound is diluted for 30 seconds, and then thoroughly dried in the shade. The dried cabbage leaves were placed on a Petri dish (diameter: 8.8 cm) which had a filter paper on, and ten 3$^{rd}$ instar larvae of *Plutella xylostella* were inoculated three times thereon. The Petri dish was stored under light condition 16:8 hours, 25±1° C. and RH 50-60%, and then the number of larvae survived were counted 24 and 48 hours after the inoculation. In some cases, the number of larvae survived were counted 72 and 96 hours after the inoculation. As shown in Equations 1 and 2, the survival rate was calculated by calibrating the larvae density after treatment with the larvae density before treatment, and the control value is calculated by subtracting the survival rate in the treatment group from the survival rate in the control group and dividing the result by the survival rate in the control group (see A method of computing the effectiveness of an insecticide. *J. Econ. Entomol.* 18: pp. 265-267, Abbott, 1925).

Control value(%)=(Survival rate in the control group–Survival rate in the treatment group)/Survival rate in the control group×100    [Equation 1]

Survival rate=larvae density after treatment/larvae density before treatment×100    [Equation 2]

The insecticidal activities of the compounds prepared in Examples 1, 2, 3 and 4 of the present application were tested in an amount of 100 ppm and the results showed that at least 80% of control values were obtained after 3 days.

Experimental Example 2

Insecticidal Activities Against Tobacco Cutworm Moth (*Spodoptera litura*) Measured by Leaf-Dip Method In this test, larvae descended from tobacco cutworm moths (*Spodoptera litura*), which had been collected in 2009 near Gyeongju area and reared in the laboratory, were used. Cabbage leaves (Dia) were cut into fragments having a diameter of 5.8 cm, immersed in a 5% acetone solution in which the test compound is diluted for 30 seconds, and then thoroughly dried in the shade. The dried cabbage leaves were placed on a Petri dish (diameter: 8.8 cm) which had a filter paper on, and ten (10) 2$^{nd}$instar larvae of *Spodoptera litura* were inoculated three times thereon. The Petri dish was stored under light condition 16:8 hours, 25±1° C. and RH 50-60%, and then the number of larvae survived were counted 24, 48, 72 and 96 hours after the inoculation. As shown in Equations 1 and 2 above, the survival rate was calculated by calibrating the larvae density after treatment with the larvae density before treatment, and the control value is calculated by subtracting the survival rate in the treatment group from the survival rate in the control group and dividing the result by the survival rate in the control group.

The insecticidal activities of the compounds prepared in Examples 4, 11, 21, 22, 33, 40, 41, 48, 51 and 54 to 64 of the present application were tested in an amount of 100 ppm and the results showed that at least 80% of percent control values were obtained after 4 days.

Experimental Example 3

Acute Toxicity Test for Honeybee (*Apis mellifera*)

The acute toxicity for honeybee was tested according to the acute contact toxicity test was conducted according to Rural Development Administration Enforcement Notification No. 2012-13 "Wildlife toxicity test standard and method—Honeybee acute toxicity test (Feb. 7, 2012)" and OECD test guideline "Honeybees, acute contact toxicity test (No. 214, adopted: 1998.09.21)."

Honeybees were purchased on Apr. 3, 2012 and raised in the room for raising honeybees located in the laboratory for about 4 months. During the breeding period, 50% sugar solution (w/w) was provided in an amount of 1 L/honey super at least once per week.

When the honeybees were raised about 4 months, at least 110% of the number of honeybees needed were moved to a breeding rack located in laboratory about 4 hours before the treatment of test compound. 10 bees were placed in each cylindrical test container made with wire mesh (height: 15 cm, diameter: 5 cm) and acclimatized to the toxicity test conditions. Honeybees were not fasted, considering the administration route of the test compounds.

Selection of honeybees for grouping was carried out by placing honeybees in an anesthetic container and putting the honeybees under anesthesia by using $CO_2$ gas. During the acclimatization period, death of honeybees, temperature and humidity were recorded. Honeybees were acclimatized in dark incubation except when being observed. During the acclimatization period, no death of honeybees was found and all honeybees were found healthy. The temperature was 24.5-25.0° C., and the humidity was 57.5-58.0%.

The 1 µL of each test compound was directly applied onto the thorax of honeybees in different concentration by using a microsyringe.

After grouping, the honeybees were put under anesthesia by placing the test container having honeybees in the anesthetic container using $CO_2$ gas. The duration of anesthesia was adjusted to 40 to 50 seconds, which was determined by the director of this experiment, and the test compounds were administered after the anesthesia.

In the toxicity test, the groups were divided into a solvent control group, a non-treatment control group, and a treatment group which was treated with 100.0 µg of the test compound/bee. A total of 30 honeybees were assigned for the test of each test compound. Mortality of honeybees and symptoms of toxicity were observed 1, 4, 24 and 48 hours after the exposure to the test compounds.

Honeybees were observed for mortality and symptoms of toxicity after 1 and 4 hours after the treatment on the date when the experiment was initiated and then observed at a 24-hour time interval until 48 hours. Death was recognized by the absence of response or the absence of movement in antennae or legs when the test organisms were mechanically stimulated. Dead organisms were not removed from the container until the experiment was completed.

No mortality was observed in the non-treatment control group, and one dead organism was found in the solvent control group. At the concentration of 100.0 µg/bee, one dead organism was observed 48 hours after the treatment.

As a result of the acute contact toxicity test of the compounds prepared in Examples of the present application, $LD_{50}$ in bees were measured as 100-200 µg/bee, which means that the test compounds are approximately 25 to 1,000 times safer for honeybees as compared to chlorantraniliprole and cyantraniliprole developed by DuPont that have $LD_{50}$ values of 0.1-4 µg/bee for honeybee.

Experimental Example 4

Log P Measurement

As shown in Equation 3 below, log P is defined as the ratio of the concentration of a compound dissolved in octanol to that dissolved in water when measured at pH in which the compound is in a neutral form.

$$\text{Log } P = \log([\text{solute}]\text{octanol}/[\text{solute}]\text{water}) \quad \text{[Equation 3]}$$

As a result of analyzing physicochemical properties of the compounds prepared in Examples of the present application, most of the compounds had log P values ranging from 1.3 to 2.0, which are at least 1.0 lower than those of chlorantraniliprole and cyantraniliprole developed by DuPont, i.e., log P values of 2.2-3.5. Generally, it is estimated that when a log P value of a compound is decreased by 0.5, the half-life of the compound is also shorten by about 3 months. Whereas chlorantraniliprole developed by DuPont having a half-life of about 180 days in soil may cause environmental risks due to its relatively long half-life in soil, the compounds of the present invention are environmentally safer owing to its rapid degradation in soil.

While the invention has been described with respect to the above specific embodiments, it should be recognized that various modifications and changes may be made to the invention by those skilled in the art which also fall within the scope of the invention as defined by the appended claims.

What is claimed is:

1. A diaminoaryl derivative represented by formula (I) or a salt thereof:

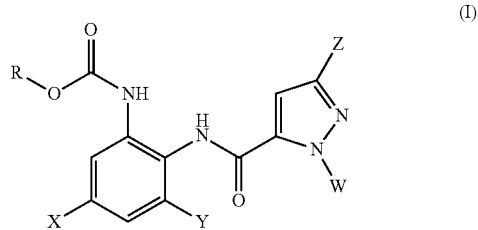

wherein X and Y are each independently hydrogen, $C_{1-6}$alkyl, $C_{2-10}$alkenyl, $C_{2-10}$alkynyl, $C_{3-6}$cycloalkyl, $C_{3-6}$cycloalkyl$C_{1-3}$alkyl, $C_{3-6}$cycloalkylamino, $C_{1-6}$alkoxy, $C_{1-5}$alkylthio, $C_{1-5}$alkylsulfinyl, $C_{1-5}$alkylsulfonyl, phenyl, phenoxy, benzyl, hydroxy, cyano, nitro or halogen, wherein each of said alkyl, alkenyl, alkynyl, cycloalkyl, alkoxy, phenyl, phenoxy and benzyl may be independently substituted with one or more halogens;

R is $C_{1-10}$alkyl, $C_{3-6}$cycloalkyl, $C_{3-6}$cycloalkyl$C_{1-3}$alkyl, $C_{2-10}$alkenyl, $C_{2-10}$alkynyl, $C_{6-12}$aryl or $C_{6-12}$ aryl$C_{1-3}$alkyl, wherein each of said alkyl, cycloalkyl, alkenyl, alkynyl and aryl may be independently substituted with 1 to 5 substituents selected from the group consisting of $C_{1-5}$alkyl, halo$C_{1-5}$alkyl, $C_{1-5}$alkoxy, halo$C_{1-5}$alkoxy, $C_{1-5}$alkylamino, $C_{1-5}$alkylimino, nitro, amino, cyano, $C_{1-5}$alkylsulfinyl, $C_{1-5}$alkylsulfonyl and halogen;

W is $C_{6-12}$aryl or 5 to 13-membered heteroaryl, wherein each of said aryl or heteroaryl may be independently substituted with 1 to 5 substituents selected from the group consisting of at least one halogen, $C_{1-4}$alkyl, $C_{2-5}$alkenyl, $C_{2-5}$alkynyl, $C_{1-4}$alkoxy, halo$C_{1-4}$alkyl, hydroxyl and cyano;

Z is halogen, cyano, amino, hydroxyl, mercapto, cyanothio, $C_{1-6}$alkyl, halo$C_{1-6}$alkyl, $C_{3-6}$cycloalkyl, $C_{3-6}$cycloalkyl$C_{1-3}$alkyl, $C_{2-6}$alkenyl, $C_{2-6}$alkynyl, $C_{1-6}$alkoxy, halo$C_{1-6}$alkoxy, $C_{1-5}$alkylthio, $C_{1-6}$alkylamino, $C_{1-6}$alkylimino, $C_{1-6}$alkylsulfinyl, $C_{1-6}$alkylsulfonyl, $C_{1-6}$alkylaminocarbonyl, —(CH$_2$)n-Q, —(CH$_2$)n-O-Q, —(CH$_2$)n-O—(CH$_2$)m-Q or —(CH$_2$)n-S-Q, wherein Q is phenyl, 5 to 10-membered heteroaryl or 5 to 10-membered heterocycloalkyl, and n and m are each independently integers of from 1 to 3; and said heteroaryl and heterocycloalkyl independently contain one to three heteroatoms selected from the group consisting of N, O and S.

2. The compound of claim 1, wherein X and Y are each independently hydrogen, $C_{1-6}$alkyl, halo$C_{1-6}$alkyl, $C_{1-6}$alkoxy, halo$C_{1-6}$alkoxy, hydroxy, cyano, nitro or halogen;

R is $C_{1-10}$alkyl, $C_{2-10}$alkenyl, $C_{6-12}$aryl or $C_{6-12}$aryl$C_{1-3}$alkyl, wherein each of said alkyl, alkenyl and aryl may independently contain 1 to 5 substituents selected from the group consisting of $C_{1-3}$alkyl, halo$C_{1-3}$alkyl, $C_{1-3}$alkoxy, halo$C_{1-3}$alkoxy, nitro and halogen;

W is $C_{6-12}$aryl, halo$C_{6-12}$aryl, 5 to 13-membered heteroaryl or 5 to 13-membered haloheteroaryl;

Z is halogen, $C_{1-6}$alkyl, halo$C_{1-6}$alkyl, $C_{1-6}$alkoxy, halo$C_{1-6}$alkoxy, cyano or $C_{1-6}$alkylaminocarbonyl; and said heteroaryl contains one to three heteroatoms selected from the group consisting of N, O and S.

3. The compound of claim 1, wherein X is hydrogen, cyano, nitro, halogen, $C_{1-5}$alkyl or halo$C_{1-5}$alkyl;

Y is $C_{1-5}$alkyl or halogen;

R is $C_{1-8}$alkyl, $C_{2-6}$alkenyl, phenyl or benzyl, wherein each of said alkyl, alkenyl, phenyl and benzyl may independently contain 1 to 3 substituents selected from the group consisting of $C_{1-3}$alkoxy, halo$C_{1-3}$alkyl, nitro and halogen;

W is phenyl, halophenyl, pyridinyl or halopyridinyl; and

Z is $C_{1-5}$alkoxy, halo$C_{1-5}$alkoxy, $C_{1-5}$alkyl, halo$C_{1-5}$alkyl, $C_{1-5}$alkylaminocarbonyl, halogen or cyano.

4. The compound of claim 1, wherein X is hydrogen, cyano, nitro, halogen or halo$C_{1-3}$alkyl;

Y is $C_{1-3}$alkyl or halogen;

R is $C_{1-8}$alkyl, $C_{2-6}$alkenyl, phenyl or benzyl, wherein each of said alkyl, alkenyl, phenyl and benzyl may independently contain 1 to 3 substituents selected from the group consisting of $C_{1-3}$alkoxy, halo$C_{1-3}$alkyl, nitro and halogen;

W is phenyl, halophenyl, pyridinyl or halopyridinyl; and

Z is $C_{1-3}$alkoxy, halo$C_{1-5}$alkoxy, halo$C_{1-3}$alkyl, $C_{1-3}$alkylaminocarbonyl, halogen or cyano.

5. The compound of claim 1, wherein the diaminoaryl derivative of formula (I) is selected from the group consisting of:

1) methyl (2-(3-bromo-1-(3-chloropyridin-2-yl)-1H-pyrazole-5-carboxamido)-3,5-dichlorophenyl)carbamate;
2) ethyl (2-(3-bromo-1-(3-chloropyridin-2-yl)-1H-pyrazole-5-carboxamido)-3,5-dichlorophenyl)carbamate;
3) isopropyl (2-(3-bromo-1-(3-chloropyridin-2-yl)-1H-pyrazole-5-carboxamido)-3,5-dichlorophenyl)carbamate;
4) isobutyl (2-(3-bromo-1-(3-chloropyridin-2-yl)-1H-pyrazole-5-carboxamido)-3,5-dichlorophenyl)carbamate;
5) butyl (2-(3-bromo-1-(3-chloropyridin-2-yl)-1H-pyrazole-5-carboxamido)-3,5-dichlorophenyl)carbamate;
6) 2-bromoethyl (2-(3-bromo-1-(3-chloropyridin-2-yl)-1H-pyrazole-5-carboxamido)-3,5-dichlorophenyl)carbamate;
7) heptyl (2-(3-bromo-1-(3-chloropyridin-2-yl)-1H-pyrazole-5-carboxamido)-3,5-dichlorophenyl)carbamate;
8) allyl (2-(3-bromo-1-(3-chloropyridin-2-yl)-1H-pyrazole-5-carboxamido)-3,5-dichlorophenyl)carbamate;
9) 2-methoxyethyl (2-(3-bromo-1-(3-chloropyridin-2-yl)-1H-pyrazole-5-carboxamido)-3,5-dichlorophenyl)carbamate;
10) 3-chloropropyl (2-(3-bromo-1-(3-chloropyridin-2-yl)-1H-pyrazole-5-carboxamido)-3,5-dichlorophenyl)carbamate;
11) methyl (2-(3-bromo-1-(3-chloropyridin-2-yl)-1H-pyrazole-5-carboxamido)-5-chloro-3-methylphenyl)carbamate;
12) isobutyl (2-(3-bromo-1-(3-chloropyridin-2-yl)-1H-pyrazole-5-carboxamido)-5-chloro-3-methylphenyl)carbamate;
13) heptyl (2-(3-bromo-1-(3-chloropyridin-2-yl)-1H-pyrazole-5-carboxamido)-5-chloro-3-methylphenyl)carbamate;
14) allyl (2-(3-bromo-1-(3-chloropyridin-2-yl)-1H-pyrazole-5-carboxamido)-5-chloro-3-methylphenyl)carbamate;
15) 2-methoxyethyl (2-(3-bromo-1-(3-chloropyridin-2-yl)-1H-pyrazole-5-carboxamido)-5-chloro-3-methylphenyl)carbamate;
16) 3-chloropropyl (2-(3-bromo-1-(3-chloropyridin-2-yl)-1H-pyrazole-5-carboxamido)-5-chloro-3-methylphenyl)carbamate;
17) 2-bromoethyl (2-(3-bromo-1-(3-chloropyridin-2-yl)-1H-pyrazole-5-carboxamido)-5-chloro-3-methylphenyl)carbamate;
18) 2,2,2-trichloroethyl (2-(3-bromo-1-(3-chloropyridin-2-yl)-1H-pyrazole-5-carboxamido)-5-chloro-3-methylphenyl)carbamate;
19) 1,1,1-trichloro-2-methylpropan-2-yl (2-(3-bromo-1-(3-chloropyridin-2-yl)-1H-pyrazole-5-carboxamido)-5-chloro-3-methylphenyl)carbamate;
20) 2-fluoroethyl (2-(3-bromo-1-(3-chloropyridin-2-yl)-1H-pyrazole-5-carboxamido)-5-chloro-3-methylphenyl)carbamate;
21) ethyl (2-(3-bromo-1-(3-chloropyridin-2-yl)-1H-pyrazole-5-carboxamido)-5-chloro-3-methylphenyl)carbamate;
22) propyl (2-(3-bromo-1-(3-chloropyridin-2-yl)-1H-pyrazole-5-carboxamido)-5-chloro-3-methylphenyl)carbamate;
23) phenyl (2-(3-bromo-1-(3-chloropyridin-2-yl)-1H-pyrazole-5-carboxamido)-5-chloro-3-methylphenyl)carbamate;
24) 4-methoxyphenyl (2-(3-bromo-1-(3-chloropyridin-2-yl)-1H-pyrazole-5-carboxamido)-5-chloro-3-methylphenyl)carbamate;
25) 4-fluorophenyl (2-(3-bromo-1-(3-chloropyridin-2-yl)-1H-pyrazole-5-carboxamido)-5-chloro-3-methylphenyl)carbamate;
26) 4-chlorophenyl (2-(3-bromo-1-(3-chloropyridin-2-yl)-1H-pyrazole-5-carboxamido)-5-chloro-3-methylphenyl)carbamate;

27) 2-chlorophenyl (2-(3-bromo-1-(3-chloropyridin-2-yl)-1H-pyrazole-5-carboxamido)-5-chloro-3-methylphenyl)carbamate;
28) 4-bromophenyl(2-(3-bromo-1-(3-chloropyridin-2-yl)-1H-pyrazole-5-carboxamido)-5-chloro-3-methylphenyl)carbamate;
29) 3-(trifluoromethyl)phenyl (2-(3-bromo-1-(3-chloropyridin-2-yl)-1H-pyrazole-5-carboxamido)-5-chloro-3-methylphenyl)carbamate;
30) benzyl (2-(3-bromo-1-(3-chloropyridin-2-yl)-1H-pyrazole-5-carboxamido)-5-chloro-3-methylphenyl)carbamate;
31) 4-nitrobenzyl (2-(3-bromo-1-(3-chloropyridin-2-yl)-1H-pyrazole-5-carboxamido)-5-chloro-3-methylphenyl)carbamate;
32) 2-chlorobenzyl (2-(3-bromo-1-(3-chloropyridin-2-yl)-1H-pyrazole-5-carboxamido)-5-chloro-3-methylphenyl)carbamate;
33) methyl (2-(3-bromo-1-(3-chloropyridin-2-yl)-1H-pyrazole-5-carboxamido)-5-cyano-3-methylphenyl)carbamate;
34) isobutyl (2-(3-bromo-1-(3-chloropyridin-2-yl)-1h-pyrazole-5-carboxamido)-5-cyano-3-methylphenyl)carbamate;
35) heptyl (2-(3-bromo-1-(3-chloropyridin-2-yl)-1H-pyrazole-5-carboxamido)-5-cyano-3-methylphenyl)carbamate;
36) allyl (2-(3-bromo-1-(3-chloropyridin-2-yl)-1H-pyrazole-5-carboxamido)-5-cyano-3-methylphenyl)carbamate;
37) 2-methoxyethyl (2-(3-bromo-1-(3-chloropyridin-2-yl)-1H-pyrazole-5-carboxamido)-5-cyano-3-methylphenyl)carbamate;
38) 3-chloropropyl (2-(3-bromo-1-(3-chloropyridin-2-yl)-1H-pyrazole-5-carboxamido)-5-cyano-3-methylphenyl)carbamate;
39) 2-bromoethyl (2-(3-bromo-1-(3-chloropyridin-2-yl)-1H-pyrazole-5-carboxamido)-5-cyano-3-methylphenyl)carbamate;
40) methyl (3,5-dibromo-2-(3-bromo-1-(3-chloropyridin-2-yl)-1H-pyrazole-5-carboxamido)phenyl)carbamate;
41) isobutyl (3,5-dibromo-2-(3-bromo-1-(3-chloropyridin-2-yl)-1H-pyrazole-5-carboxamido)phenyl)carbamate;
42) heptyl (3,5-dibromo-2-(3-bromo-1-(3-chloropyridin-2-yl)-1H-pyrazole-5-carboxamido)phenyl)carbamate;
43) allyl (3,5-dibromo-2-(3-bromo-1-(3-chloropyridin-2-yl)-1H-pyrazole-5-carboxamido)phenyl)carbamate;
44) 2-methoxyethyl (3,5-dibromo-2-(3-bromo-1-(3-chloropyridin-2-yl)-1H-pyrazole-5-carboxamido)phenyl)carbamate;
45) 3-chloropropyl (3,5-dibromo-2-(3-bromo-1-(3-chloropyridin-2-yl)-1H-pyrazole-5-carboxamido)phenyl)carbamate;
46) 2-bromoethyl (3,5-dibromo-2-(3-bromo-1-(3-chloropyridin-2-yl)-1H-pyrazole-5-carboxamido)phenyl)carbamate;
47) isobutyl (5-bromo-2-(3-bromo-1-(3-chloropyridin-2-yl)-1H-pyrazole-5-carboxamido)-3-methylphenyl)carbamate;
48) methyl (2-(3-bromo-1-(3-chloropyridin-2-yl)-1H-pyrazole-5-carboxamido)-3-chloro-5-(trifluoromethyl)phenyl)carbamate;
49) isobutyl (2-(3-bromo-1-(3-chloropyridin-2-yl)-1H-pyrazole-5-carboxamido)-3-chloro-5-(trifluoromethyl)phenyl)carbamate;
50) heptyl (2-(3-bromo-1-(3-chloropyridin-2-yl)-1H-pyrazole-5-carboxamido)-3-chloro-5-(trifluoromethyl)phenyl)carbamate;
51) methyl (3-bromo-2-(3-bromo-1-(3-chloropyridin-2-yl)-1H-pyrazole-5-carboxamido)-5-(trifluoromethyl)phenyl)carbamate;
52) isobutyl (3-bromo-2-(3-bromo-1-(3-chloropyridin-2-yl)-1H-pyrazole-5-carboxamido)-5-(trifluoromethyl)phenyl)carbamate;
53) heptyl (3-bromo-2-(3-bromo-1-(3-chloropyridin-2-yl)-1H-pyrazole-5-carboxamido)-5-(trifluoromethyl)phenyl)carbamate;
54) methyl (2-(3-bromo-1-(3-chloropyridin-2-yl)-1H-pyrazole-5-carboxamido)-3-methylphenyl)carbamate;
55) methyl (2-(3-bromo-1-(3-chloropyridin-2-yl)-1H-pyrazole-5-carboxamido)-3-methyl-5-nitrophenyl)carbamate;
56) methyl (2-(3-chloro-1-(3-chloropyridin-2-yl)-1H-pyrazole-5-carboxamido)-5-cyano-3-methylphenyl)carbamate;
57) methyl (2-(1-(3-chloropyridin-2-yl)-3-cyano-1H-pyrazole-5-carboxamido)-5-cyano-3-methylphenyl)carbamate;
58) methyl (2-(1-(3-chloropyridin-2-yl)-3-methoxy-1H-pyrazole-5-carboxamido)-5-cyano-3-methylphenyl)carbamate;
59) methyl (2-(1-(3-chloropyridin-2-yl)-$N^3$-methyl-1H-pyrazole-3,5-dicarboxamido)-5-cyano-3-methylphenyl)carbamate;
60) methyl (2-(3-(2,2,2-trifluoroethoxy)-1-(3-chloropyridin-2-yl)-1H-pyrazole-5-carboxamido)-5-cyano-3-methylphenyl)carbamate;
61) methyl (2-(1-(3-chloropyridin-2-yl)-3-(trifluoromethyl)-1H-pyrazole-5-carboxamido)-5-cyano-3-methylphenyl)carbamate;
62) methyl (2-(1-(2-chlorophenyl)-3-(trifluoromethyl)-1H-pyrazole-5-carboxamido)-5-cyano-3-methylphenyl)carbamate;
63) ethyl (2-(3-bromo-1-(3-chloropyridin-2-yl)-1H-pyrazole-5-carboxamido)-5-cyano-3-methylphenyl)carbamate; and
64) 2-chloroethyl (2-(3-bromo-1-(3-chloropyridin-2-yl)-1H-pyrazole-5-carboxamido)-5-cyano-3-methylphenyl)carbamate.

6. An insecticidal composition comprising the compound of claim 1 as an active ingredient.

7. A method of controlling harmful insects by applying the compound of claim 1 to crops or crop fields.

8. An insecticidal composition comprising the compound of claim 2 as an active ingredient.

9. An insecticidal composition comprising the compound of claim 3 as an active ingredient.

10. An insecticidal composition comprising the compound of claim 4 as an active ingredient.

11. An insecticidal composition comprising the compound of claim 5 as an active ingredient.

12. A method of controlling harmful insects by applying the compound of claim 2 to crops or crop fields.

13. A method of controlling harmful insects by applying the compound of claim 3 to crops or crop fields.

14. A method of controlling harmful insects by applying the compound of claim 4 to crops or crop fields.

15. A method of controlling harmful insects by applying the compound of claim 5 to crops or crop fields.

* * * * *